(12) United States Patent
Butterman et al.

(10) Patent No.: US 8,057,549 B2
(45) Date of Patent: Nov. 15, 2011

(54) APPARATUS AND METHOD FOR PERFORMING SPINAL SURGERY

(75) Inventors: Glenn Robin Butterman, Mahtomedi, MN (US); Jeffrey Joseph Anderman, Solana Beach, CA (US); Frank Robert Ferris, Jr., Bellevue, WA (US)

(73) Assignee: Dynamic Spine, Inc., Solana Beach, CA (US)

( * ) Notice: Subject to any disclaimer, the term of this patent is extended or adjusted under 35 U.S.C. 154(b) by 299 days.

(21) Appl. No.: 11/948,427

(22) Filed: Nov. 30, 2007

(65) Prior Publication Data

US 2008/0215153 A1 Sep. 4, 2008

Related U.S. Application Data

(63) Continuation of application No. 10/913,510, filed on Aug. 9, 2004, now abandoned.

(60) Provisional application No. 60/492,966, filed on Aug. 7, 2003, provisional application No. 60/512,186, filed on Oct. 20, 2003.

(51) Int. Cl.
*A61F 2/44* (2006.01)

(52) U.S. Cl. ............... 623/17.16; 623/17.13; 623/17.14; 623/17.15

(58) Field of Classification Search ............... 623/17.13, 623/17.14, 17.15, 17.16
See application file for complete search history.

(56) References Cited

U.S. PATENT DOCUMENTS

| | | | |
|---|---|---|---|
| 3,426,364 A | 2/1969 | Lumb | |
| 4,242,758 A | 1/1981 | Amis et al. | |
| 4,309,777 A | 1/1982 | Patil | |
| 4,553,273 A * | 11/1985 | Wu | 623/23.45 |
| 4,586,496 A | 5/1986 | Keller | |
| 4,697,586 A | 10/1987 | Gazale | |
| D295,317 S | 4/1988 | Gazale | |
| D295,318 S | 4/1988 | Gazale | |
| 4,759,766 A * | 7/1988 | Buettner-Janz et al. | 623/17.15 |
| 4,759,769 A * | 7/1988 | Hedman et al. | 623/17.13 |

(Continued)

FOREIGN PATENT DOCUMENTS

DE 90 00 094.3 U1 3/1991

(Continued)

OTHER PUBLICATIONS

European Search Report corresponding to EP 04786456.6, dated Sep. 14, 2009, 3 pages.

(Continued)

*Primary Examiner* — Thomas J Sweet
*Assistant Examiner* — Christopher D Prone
(74) *Attorney, Agent, or Firm* — Foley & Lardner LLP

(57) ABSTRACT

An embodiment of an intervertebral prosthetic device for implantation in a spine includes a rigid fixation member and a compressible member. The fixation member is configured to be placed in a cavity of a first vertebral body and against bone of the first vertebral body. The compressible member is configured to be placed in a cavity in an intervertebral disc and to be secured to the first fixation member. Another embodiment includes two compressible members and one fixation member. In this embodiment, the first and second compressible members are sized to substantially replace the nucleus pulposus of first and a second intervertebral discs, respectively, on either side of a vertebral body. The fixation member is sized to fit within a cavity in the vertebral body between the first and second compressible members.

57 Claims, 29 Drawing Sheets

U.S. PATENT DOCUMENTS

| | | | |
|---|---|---|---|
| 4,787,377 A | 11/1988 | Laboureau | |
| 4,911,718 A | 3/1990 | Lee et al. | |
| 4,932,975 A | 6/1990 | Main et al. | |
| 4,936,856 A | 6/1990 | Keller | |
| 5,002,576 A | 3/1991 | Fuhrmann et al. | |
| 5,015,255 A | 5/1991 | Kuslich | |
| 5,047,055 A | 9/1991 | Bao et al. | |
| 5,055,104 A | 10/1991 | Ray | |
| 5,059,193 A | 10/1991 | Kuslich | |
| 5,062,845 A | 11/1991 | Kuslich et al. | |
| 5,071,437 A | 12/1991 | Steffee | |
| 5,108,438 A | 4/1992 | Stone | |
| 5,123,926 A | 6/1992 | Pisharodi | |
| 5,141,513 A | 8/1992 | Fortune et al. | |
| 5,171,278 A | 12/1992 | Pisharodi | |
| 5,236,460 A | 8/1993 | Barber | |
| 5,246,458 A | 9/1993 | Graham | |
| 5,290,312 A | 3/1994 | Kojimoto et al. | |
| 5,306,310 A | 4/1994 | Siebels | |
| 5,314,477 A | 5/1994 | Marnay | |
| 5,336,223 A | 8/1994 | Rogers | |
| 5,360,430 A | 11/1994 | Lin | |
| 5,375,823 A | 12/1994 | Navas | |
| 5,390,683 A | 2/1995 | Pisharodi | |
| 5,397,359 A | 3/1995 | Mittelmeier et al. | |
| 5,405,391 A | 4/1995 | Hednerson et al. | |
| 5,423,816 A | 6/1995 | Lin | |
| 5,433,005 A | 7/1995 | Cogdill et al. | |
| 5,445,639 A | 8/1995 | Kuslich et al. | |
| 5,458,638 A | 10/1995 | Kuslich et al. | |
| 5,458,641 A | 10/1995 | Ramirez Jimenez | |
| 5,458,642 A | 10/1995 | Beer et al. | |
| 5,480,401 A | 1/1996 | Navas | |
| 5,480,442 A | 1/1996 | Bertagnoli | |
| 5,489,307 A | 2/1996 | Kuslich et al. | |
| 5,489,308 A | 2/1996 | Kuslich et al. | |
| 5,490,860 A | 2/1996 | Middle et al. | |
| 5,514,139 A | 5/1996 | Goldstein et al. | |
| 5,549,679 A | 8/1996 | Kuslich | |
| 5,571,189 A | 11/1996 | Kuslich | |
| 5,591,235 A | 1/1997 | Kuslich | |
| 5,597,379 A | 1/1997 | Haines et al. | |
| 5,723,013 A * | 3/1998 | Jeanson et al. | 623/17.16 |
| 5,782,832 A | 7/1998 | Larsen et al. | |
| 5,810,827 A | 9/1998 | Haines et al. | |
| 5,827,328 A | 10/1998 | Buttermann | |
| 5,873,579 A | 2/1999 | Prokop et al. | |
| 5,893,889 A | 4/1999 | Harrington | |
| 5,897,590 A | 4/1999 | Donovan | |
| 5,928,284 A | 7/1999 | Mehdizadeh | |
| 5,951,553 A | 9/1999 | Betz et al. | |
| 5,961,522 A | 10/1999 | Mehdizadeh | |
| 5,989,256 A | 11/1999 | Kuslich et al. | |
| 6,039,763 A | 3/2000 | Shelokov | |
| 6,056,749 A | 5/2000 | Kuslich | |
| 6,056,754 A | 5/2000 | Haines et al. | |
| 6,063,121 A | 5/2000 | Xavier et al. | |
| 6,086,589 A | 7/2000 | Kuslich et al. | |
| 6,110,175 A | 8/2000 | Scholl | |
| 6,132,151 A | 10/2000 | Courmier | |
| 6,162,252 A | 12/2000 | Kuras et al. | |
| 6,174,311 B1 | 1/2001 | Branch et al. | |
| 6,209,886 B1 | 4/2001 | Estes et al. | |
| 6,231,609 B1 | 5/2001 | Mehdizadeh | |
| 6,264,695 B1 | 7/2001 | Stoy | |
| 6,287,308 B1 | 9/2001 | Betz et al. | |
| 6,315,797 B1 * | 11/2001 | Middleton | 623/17.16 |
| 6,383,188 B2 | 5/2002 | Kuslich et al. | |
| 6,419,704 B1 | 7/2002 | Ferree | |
| 6,454,806 B1 | 9/2002 | Cohen et al. | |
| 6,517,544 B1 | 2/2003 | Michelson | |
| 6,520,996 B1 | 2/2003 | Manasas et al. | |
| 6,527,804 B1 | 3/2003 | Gauchet et al. | |
| 6,551,320 B2 | 4/2003 | Lieberman | |
| 6,558,386 B1 | 5/2003 | Cragg | |
| 6,558,390 B2 | 5/2003 | Cragg | |
| 6,572,653 B1 | 6/2003 | Simonson | |
| 6,575,978 B2 | 6/2003 | Peterson et al. | |
| 6,576,016 B1 | 6/2003 | Hochshuler et al. | |
| 6,582,468 B1 | 6/2003 | Gauchet | |
| 6,589,281 B2 | 7/2003 | Hyde, Jr. | |
| 6,605,648 B1 | 8/2003 | Johnson et al. | |
| 6,607,558 B2 | 8/2003 | Kuras | |
| 6,607,559 B2 | 8/2003 | Ralph et al. | |
| 6,610,093 B1 * | 8/2003 | Pisharodi | 623/17.15 |
| 6,645,249 B2 | 11/2003 | Ralph et al. | |
| 6,669,730 B2 | 12/2003 | Ralph et al. | |
| 6,673,113 B2 | 1/2004 | Ralph et al. | |
| 6,716,249 B2 | 4/2004 | Hyde | |
| 6,719,796 B2 | 4/2004 | Cohen et al. | |
| 6,733,532 B1 | 5/2004 | Gauchet et al. | |
| 6,740,117 B2 | 5/2004 | Ralph et al. | |
| 6,761,723 B2 | 7/2004 | Buttermann et al. | |
| 6,869,445 B1 | 3/2005 | Johnson | |
| 2001/0049527 A1 | 12/2001 | Cragg | |
| 2002/0016583 A1 | 2/2002 | Cragg | |
| 2002/0055740 A1 | 5/2002 | Lieberman | |
| 2002/0058944 A1 | 5/2002 | Michelson | |
| 2003/0009224 A1 | 1/2003 | Kuras | |
| 2003/0236571 A1 | 12/2003 | Ralph et al. | |
| 2004/0002761 A1 | 1/2004 | Rogers et al. | |
| 2004/0024461 A1 | 2/2004 | Ferree | |
| 2004/0034421 A1 | 2/2004 | Errico et al. | |
| 2004/0034426 A1 | 2/2004 | Errico et al. | |
| 2004/0039448 A1 | 2/2004 | Pisharodi | |
| 2004/0044410 A1 | 3/2004 | Ferree et al. | |
| 2004/0102849 A1 | 5/2004 | Ralph et al. | |
| 2004/0111155 A1 | 6/2004 | Ferree | |
| 2004/0111156 A1 | 6/2004 | Ralph et al. | |

FOREIGN PATENT DOCUMENTS

| | | |
|---|---|---|
| DE | 94 13 778 U1 | 2/1996 |
| EP | 0 577 178 A1 | 1/1994 |
| EP | 0 948 299 B1 | 10/1999 |
| FR | 2799638 | 4/2001 |
| JP | 1-308557 | 12/1989 |
| JP | 5-277141 | 10/1993 |
| JP | 5-317407 | 12/1993 |
| JP | 5-508795 | 12/1993 |
| RU | 2008851 C1 | 3/1994 |
| WO | WO 91/06266 | 5/1991 |
| WO | WO 92/10982 | 7/1992 |
| WO | WO 95/19153 | 7/1995 |
| WO | WO 96/28118 | 9/1996 |
| WO | WO 02/09626 A1 | 2/2002 |
| WO | WO 03/059177 A1 | 7/2003 |

OTHER PUBLICATIONS

"U.S. Markets for Adjunctive and Non-Fusion Spine Technologies", *Health Research International Division of Personal Medical Systems, Inc.*, Report #103-1-US-0103, Jan. 2003, pp. 5-1 through 5-84.

G. Cinotti et al., "Results of Disc Prosthesis After a Minimum Follow-Up Period of 2 Years", *Spine,* 1996, vol. 21, No. 8, pp. 995-1000, Lippincott-Raven Publishers.

M. de Kleuver et al., "Total Disc Replacement for Chronic Low Back Pain: Background and a Systematic Review of the Literature", *Eur Spin J,* 2003, vol. 12, pp. 108-116.

Von Karin Büttner-Janz et al., "Bandscheibenendoprothetik Entwicklungsweg und gegenwärtiger Stand", *Beitr. Orthop. Traumatol.*, vol. 37, H. 3, Mar. 1990, pp. 137-147.

C. K. Lee et al., "Development of a Prosthetic Intervertebral Disc", *Spine*, 1991, vol. 16, No. 6 supp., pp. S253-S255.

H. Tsuji et al., "Artificial Ceramic Intervertebral Disc Replacement in Cervical Disc Lesion", *J. West. Pac. Orthop. Assoc.*, 1990, vol. 27, No. 1, pp. 101-106.

S. K. Schmiedberg et al., "Isolation and Characterization of Metallic Wear Debris from a Dynamic Intervertebral Disc Prosthesis", *J. of Biomed. Materials Res.*, 1994, vol. 28, pp. 1277-1288.

A. D. Stefee, "The Steefee Artificial Disc" *Clinical Efficacy and Outcome in the Diagnosis and Treatment of Low Back Pain*, 1992, Chapter 24, pp. 245-257.

N.A. Langrana et al., "Finite-Element Modeling of the Synthetic Intervertebral Disc", *Spine*, vol. 16, No. 6 supp., 1991, pp. S245-S252.

K. Büttner-Janz et al., "Biomechanics of the SB Charité Lumbar Intervertebral Disc Endoprosthesis", *International Orthopeadics (SICOT)*, 1989, vol. 13, pp. 173-176.

P. Enker et al., "Artificial Disc Replacement", *Spine,* 1993, vol. 18, No. 8, pp. 1061-1070.

T. P. Hedman et al., "Design of an Intervertebral Disc Prosthesis", *Spine*, 1991, vol. 16, No. 6 supp., pp. S256-S260.

W.G. Hellier et al., "Wear Studies for Development of an Intervertebral Disc Prosthesis", *Spine,* 1992, vol. 17, No. 6 suppl., pp. S86-S96.

H. Tie-Sheng et al., "Lumbar Intervertebral Disc Prosthesis", *Chin. Med. J.*, 1991, vol. 104, No. 5, pp. 381-386.

S. L. Griffith et al., "A Multicenter Retrospective Study of the Clinical Results of the LINK® SB Charité Intervertebral Prosthesis", *Spine*, vol. 19, No. 16, pp. 1842-1849.

J. P. Kostuik, "The Kostuik Artificial Disc", *Clinical Efficacy and Outcome in the Diagnosis and Treatment of Low Back Pain*, 1992, Chapter 25, pp. 259-270.

C. K. Lee et al., Relative Efficacy of the Artificial Disc Versus Spinal Fusion, *Clinical Efficacy and Outcome in the Diagnosis and Treatment of Low Back Pain*, 1992, Chapter 23, pp. 237-243.

C. D. Ray, "The Artificial Disc Intraduction, History, and Socioecnomics", *Clinical Efficacy and Outcome in the Diagnosis and Treatment of Low Back Pain*, 1992, Chapter 21, pp. 205-225.

H. G. Edland, "Some Additional Suggestions for an Intervertebral Disc Prosthesis", *J. Biomed Eng.*, Jan. 1985, vol. 7, pp. 57-62.

J. R. Urbaniak et al., "Replacement of Intervertebral Discs in Chimpanzees by Silicone-Dacron Implants: A Preliminary Report", *J. Biomed. Mater. Res. Symposium*, 1973, vol. 7, No. 4, pp. 165-186.

U. Fernström, "Arthroplasty with Intercorporal Endoprothesis in Herniated Disc and in Painful Disc", *Acta Chir Scand*, 1966, vol. 357 supp., pp. 154-159.

B. Fassio et al., "Prothères Discale en Silicone. Etude Expèrimentale et Premiéres Observations Cliniques", *La Nouvelle Presse Médicale*, Jan. 21, 1978, vol. 7, No. 3, p. 207.

U. Fernström, "Intradiskal Endoprotes av Metall vid Lumbala Och Cervicala Diskrupturer", *Nordisk Medicin*, 1965, vol. 73, No. 11, pp. 272-273.

H. G. Edeland, "Suggestions for a Total Elasto-Dynamic Intervertebral Disc Prosthesis", *Biomat. Med. Dev. Art. Org.*, 1981, vol. 9, No. 1, pp. 65-72.

"Compressors and Distractors", Spine Surgical Innovation, South Easton, MA., available prior to Aug. 7, 2003.

M. Kanayama et al., "Intraoperative Biomechanical Assessment of Lumbar Spinal Instability: Validation of Radiographic Parameters Indicating Anterior Column Support in Lumbar Spinal Fusion", *Spine*, vol. 28, pp. 2368-2372 (2003).

Scott Hensley, "Artificial Spinal Disc May Open New Era in Treating Back Pain, But Worries Linger", The Wall Street Journal, Personal Journal, p. D1, Nov. 2, 2004.

M. D. Brown, et al., "Intraoperative Measurement of Functional Spine Unit Stiffness", University of Miami School of Medicine, Department of Orthopaedics and Rehabilitation (R-2), 5 pp., Spinal Stiffness Gauge—ORS Abstract 1998, http://www.mekanika.com/htm/abstract/orsabstr.html printed from website on Oct. 30, 2001.

"The Spinal Stabilization Company", Mekanika, 42 pp., www.mekanika.com printed from website on Aug. 9, 2005.

"The First Real Systems Solution to Correcting Spinal Instability," Mekanika, 6 pp., available prior to Aug. 7, 2003.

"The Trephine System", Trephine System Technique Guide, pp. 1-11, available prior to Aug. 7, 2003.

H. Mathews, et al., "Precision-Graft™ Anterior Impacted Instrumentation Set Surgical Technique", Medtronic Sofamor Danek, pp. 1, 13, 16, 44, available prior to Aug. 7, 2003.

Mark D. Brown et al., "Measurement of Cadaver Lumbar Spine Motion Segment Stiffness", *Spine*, vol. 27, No. 9, pp. 918-922 (2002).

Neuro, Ortho & Spinal Surgery, SSI Ultra Instruments Catalog, pp. 1, www.specsurg.com/ultra/Neuro.cfm printed from website Aug. 10, 2005.

Noshir A. Langrana et al., "Materials and Design Concepts for an Intervertebral Disc Spacer. I. Fiber-Reinforced Composite Design", Journal of Applied Biomaterials, vol. 5, pp. 125-132, 1994.

"FDA Approves Artificial Disc; Another Alternative to Treat Low Back Pain," FDA Talk Paper, T04-45, Oct. 26, 2004.

Red Herring The Business of Technology, "Easing Back and Joint Pain", www.redherring.com, Mar. 6, 2006.

* cited by examiner

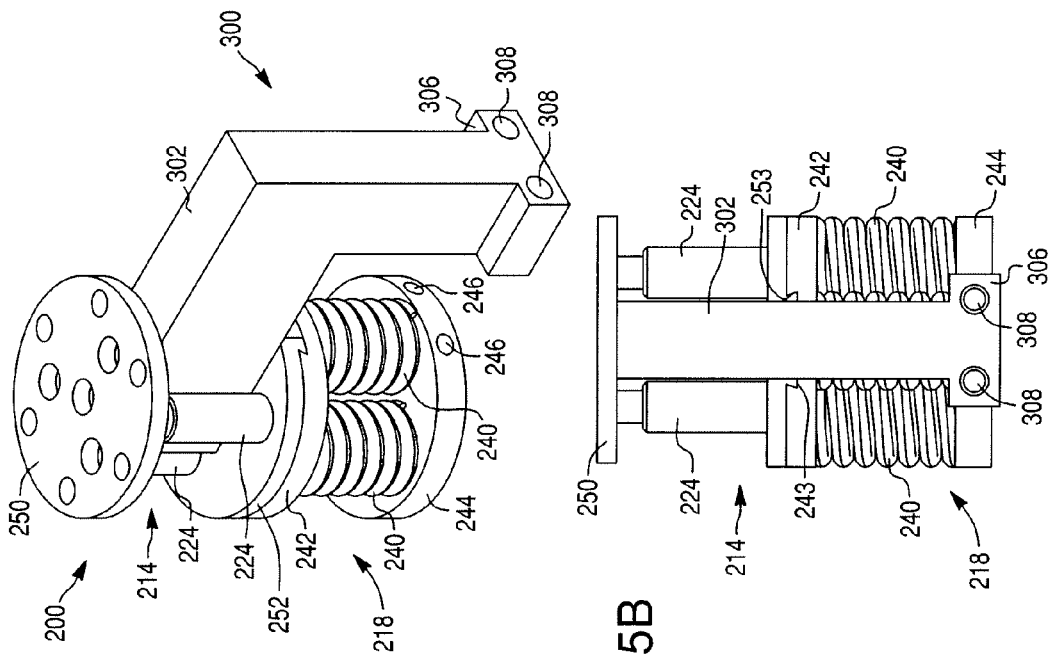
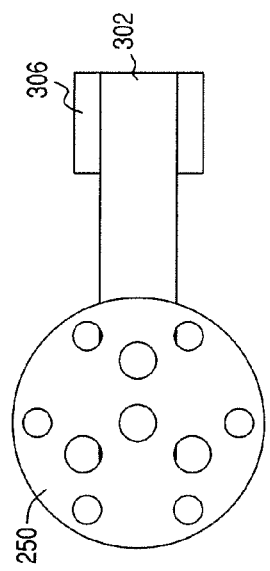
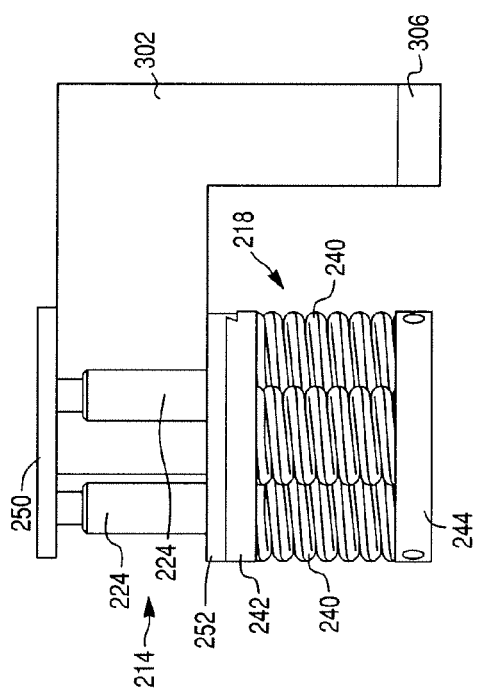
Fig. 15A  Fig. 15B  Fig. 15C  Fig. 15D

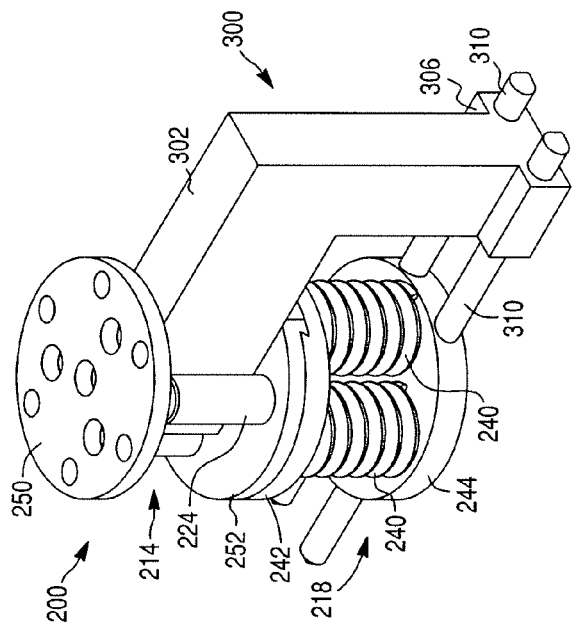
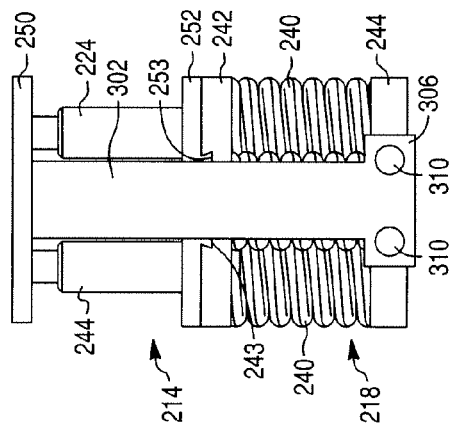
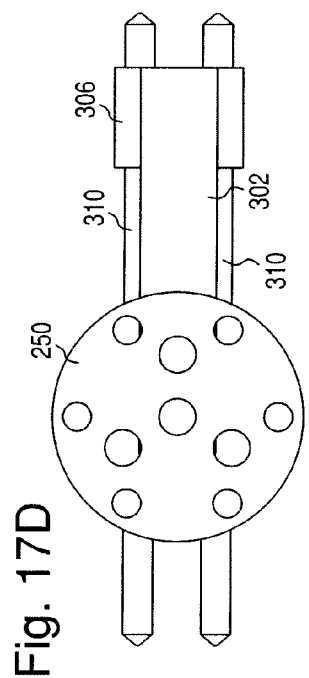
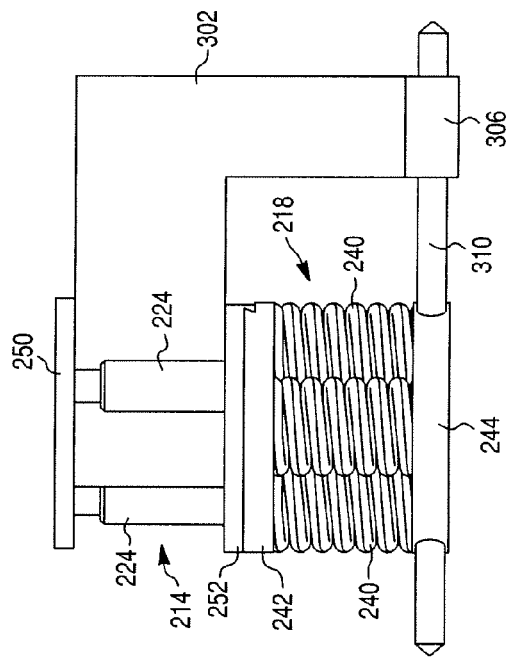
Fig. 17A
Fig. 17B
Fig. 17D
Fig. 17C

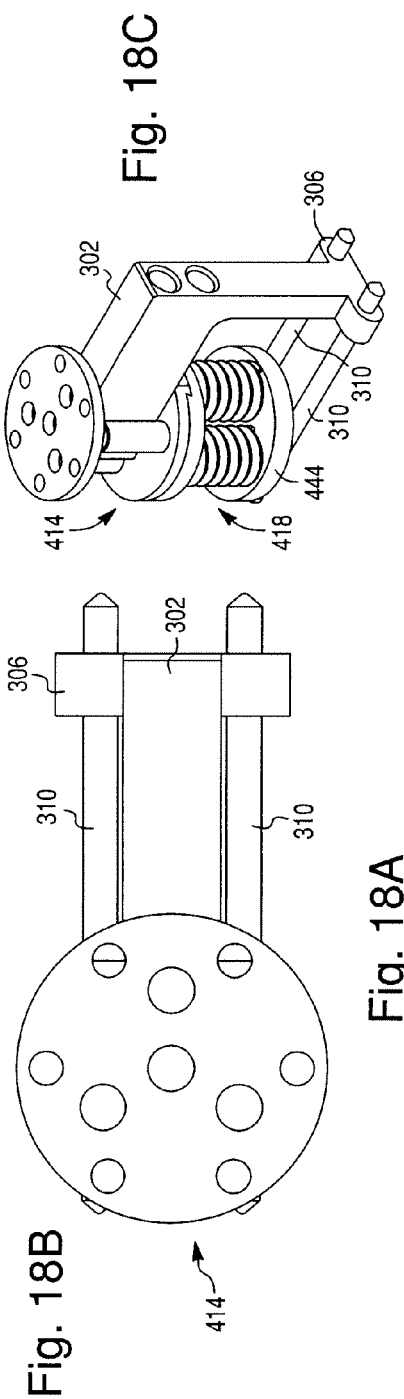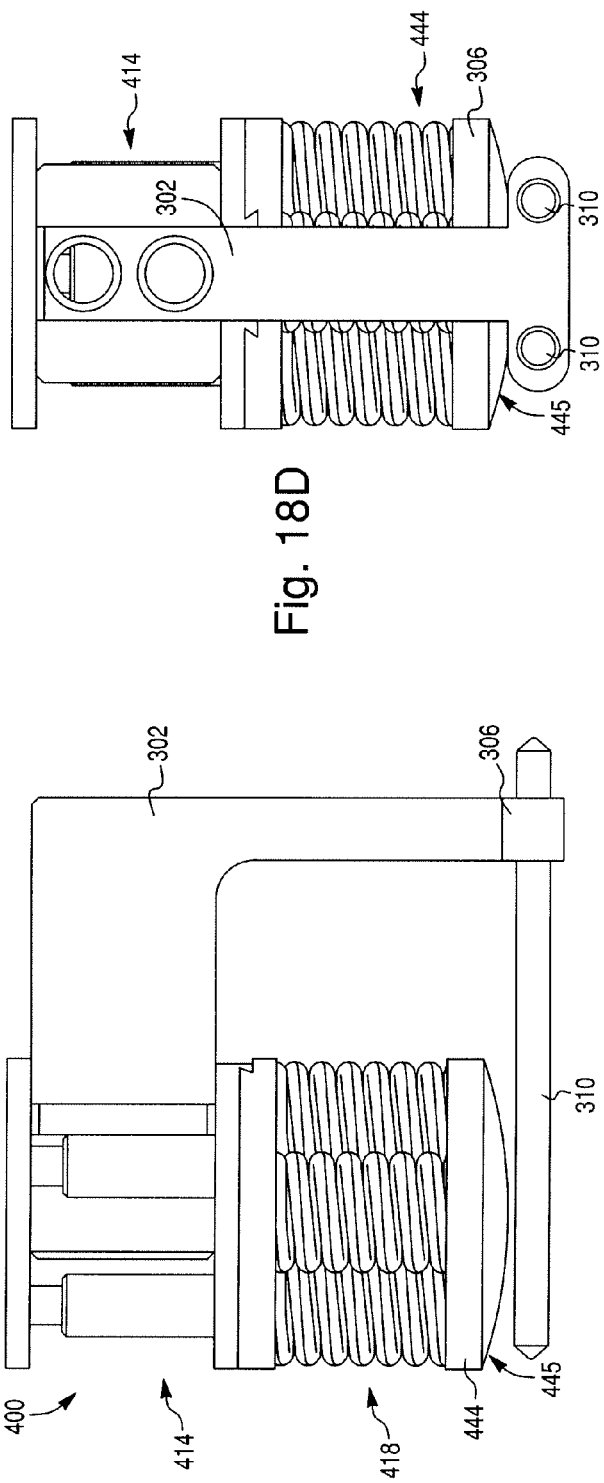

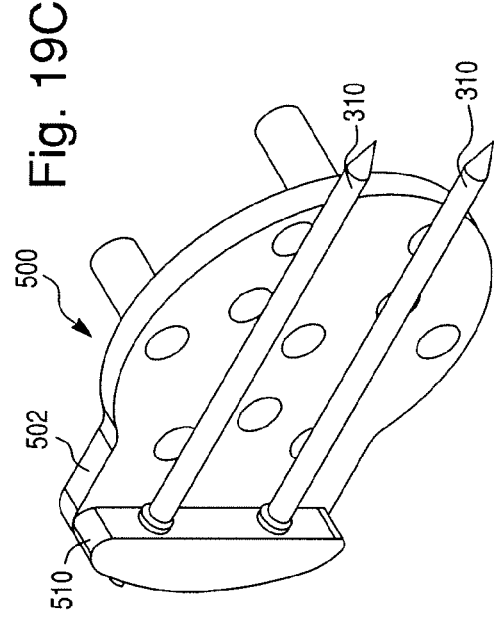
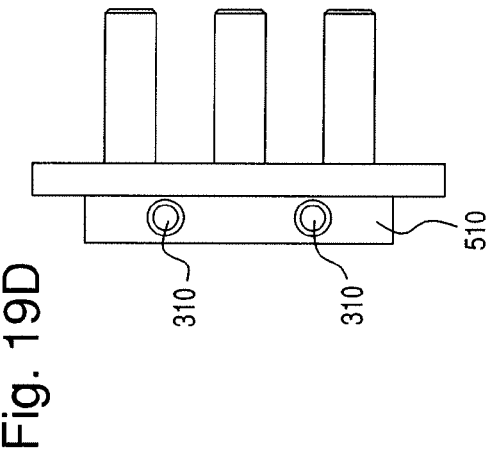
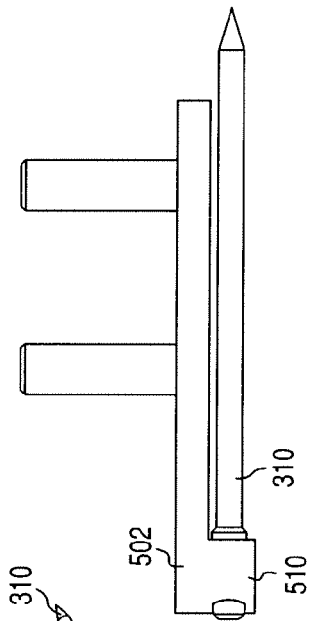
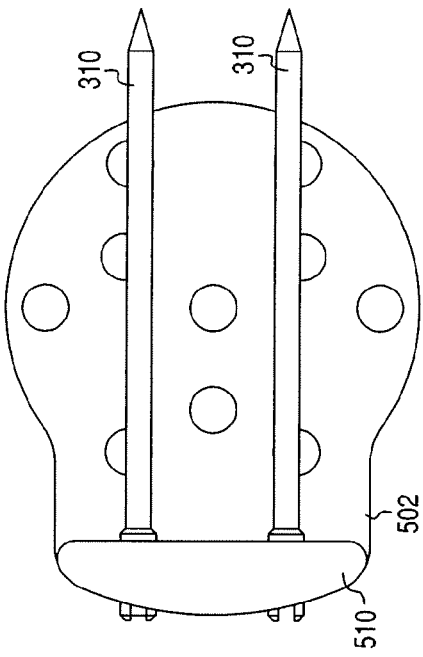

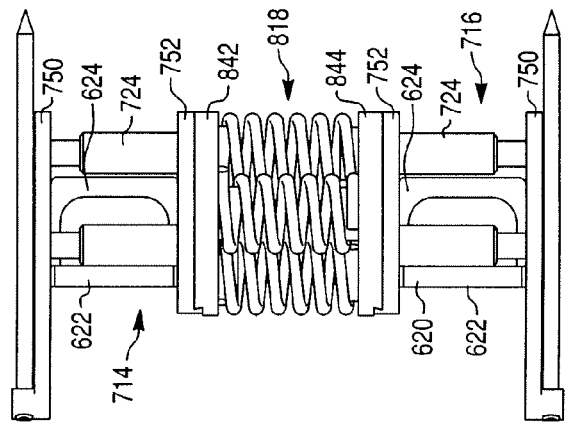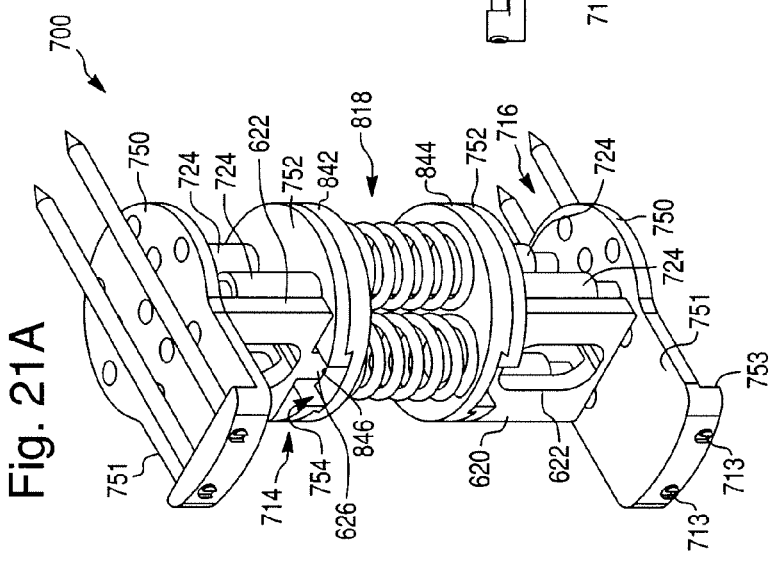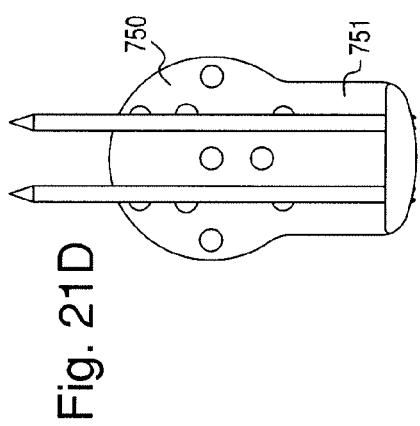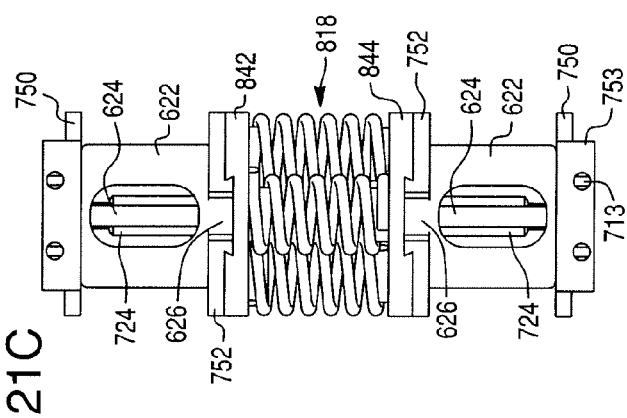

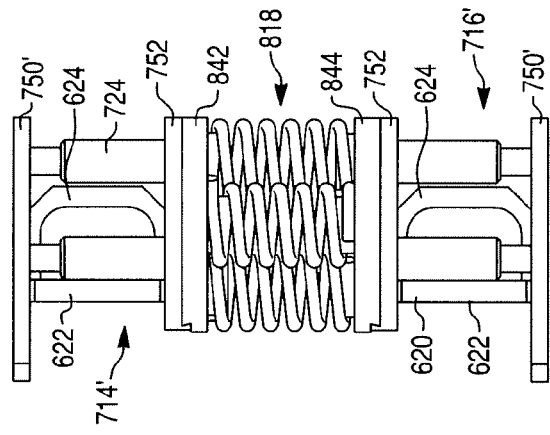
Fig. 22B
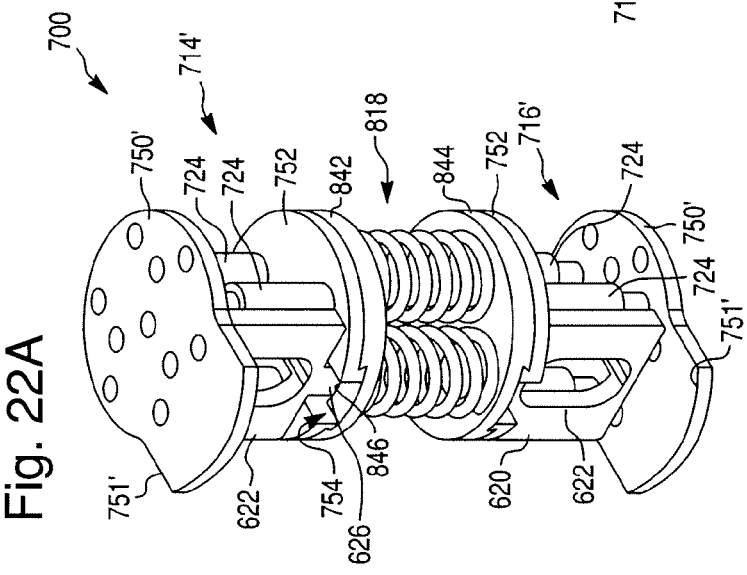
Fig. 22A
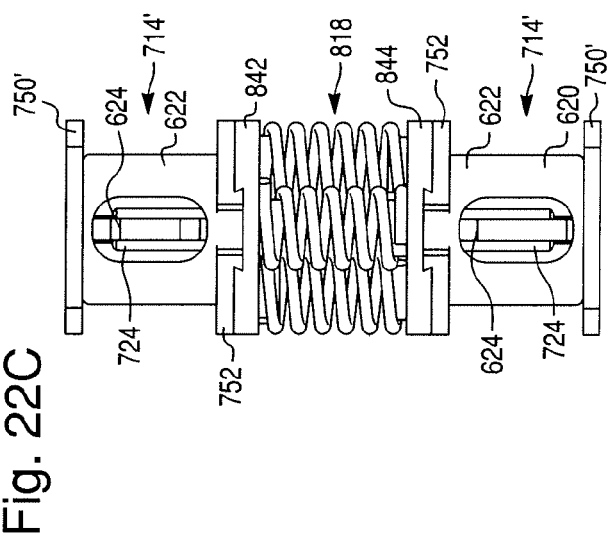
Fig. 22D
Fig. 22C

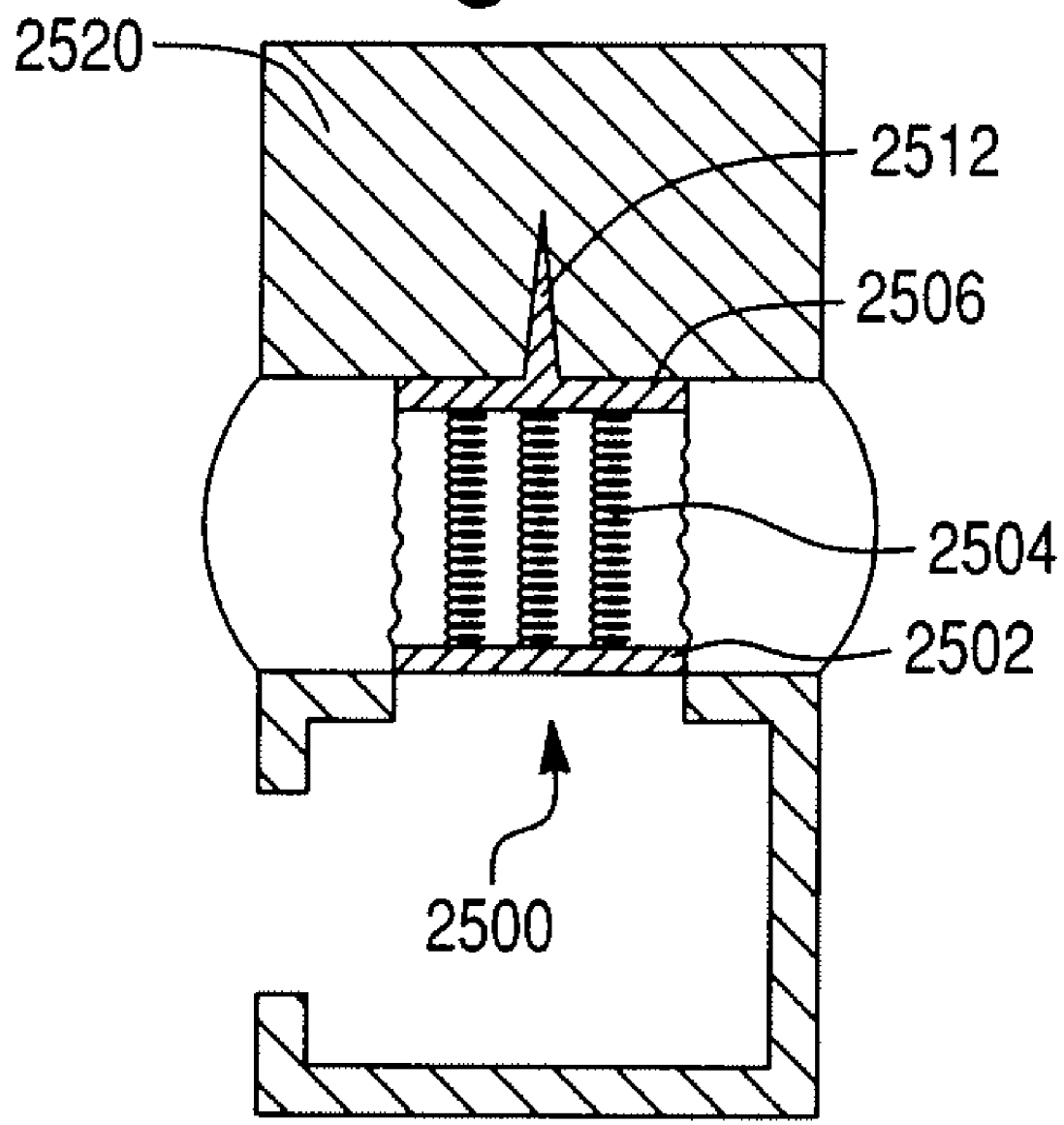

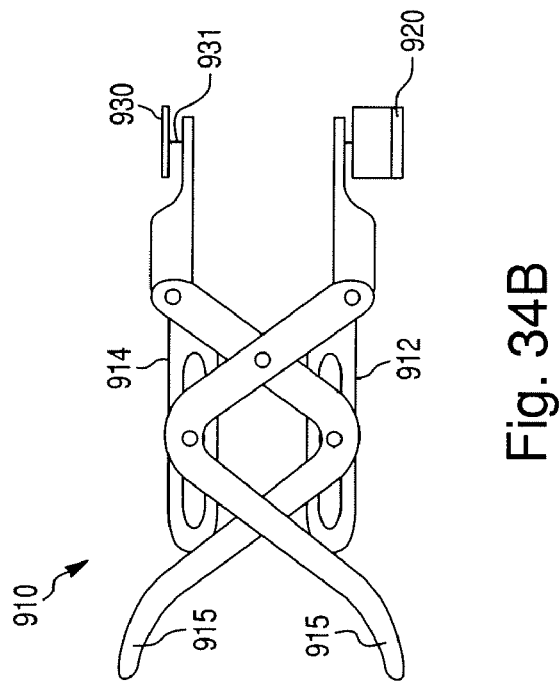
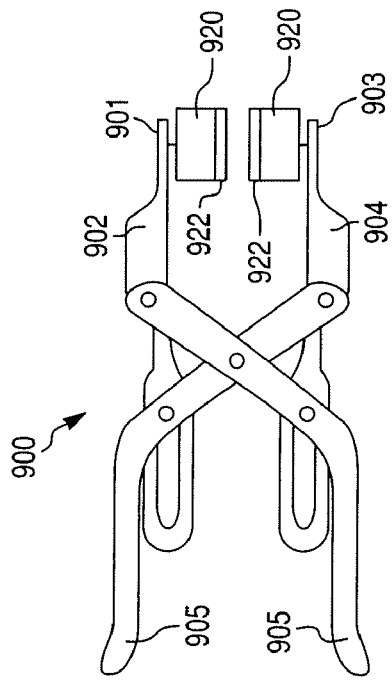

APPARATUS AND METHOD FOR PERFORMING SPINAL SURGERY

CROSS-REFERENCE TO RELATED APPLICATIONS

This application is a continuation of U.S. patent application Ser. No. 10/913,510, filed Aug. 9, 2004 which claims priority to U.S. provisional patent application Ser. Nos. 60/492,966, filed Aug. 7, 2003 and 60/512,186, filed Oct. 20, 2003.

BACKGROUND

This invention relates to the field of spinal surgery. More specifically, this invention relates to a novel implantable apparatus for replacing the functionality of one or more failing intervertebral discs, without fusing the vertebral bodies above and below the disc(s). This invention also relates to devices for implanting and securing the intervertebral prosthetic device in cavities in a vertebral body and in one or more adjacent intervertebral discs. The invention further relates to methods for performing spinal surgery.

The human spine is a flexible structure comprised of twenty-three mobile vertebrae. Intervertebral discs separate and cushion adjacent vertebrae. The top and bottom surfaces of intervertebral discs abut vertebral body endplates. The intervertebral discs act as shock absorbers and allow bending between the vertebrae.

An intervertebral disc comprises two major components: the nucleus pulposus and the annulus fibrosis. The nucleus pulposus is centrally located in the disc and occupies 25-40% of the disc's total cross-sectional area. The nucleus pulposus usually contains 70-90% water by weight and mechanically functions like an incompressible hydrostatic material. The annulus fibrosis surrounds the nucleus pulposus and resists torsional and bending forces applied to the disc. Thus, the annulus fibrosis serves as the disc's main stabilizing structure. A healthy disc relies on the unique relationship of the nucleus and annulus to one another.

Individuals with damaged or degenerated discs often experience significant pain. The pain results, in part, from instability in the intervertebral joint due to a loss of hydrostatic pressure in the nucleus pulposus, which leads to a loss of disc height and altered loading of the annulus fibrosis.

A conventional treatment for degenerative disc disease is spinal fusion. In one such surgical procedure, a surgeon removes the damaged natural disc and then fuses the two adjacent vertebral bodies into one piece. The surgeon fuses the vertebral bodies by grafting bone between the adjacent vertebrae and sometimes using metal rods, cages, or screws to hold the graft in place until the graft heals.

Although spinal fusion may alleviate pain associated with degenerative disc disease, it also results in loss of motion at the fused vertebral joint. Lack of motion at the fused site puts additional stress on the discs above and below the fusion. The additional stress may cause the adjacent discs to degenerate and produce pain, thereby recreating the original problem.

To remedy the problems associated with spinal fusion, various prosthetic devices have been developed either to replace the entire disc (i.e., the nucleus pulposus and the annulus fibrosis) with a prosthetic joint or to replace the nucleus pulposus of the damaged disc with a suitable biomechanical equivalent. Unfortunately, the previous approaches have certain limitations because conventional total disc replacement devices and nucleus replacement devices disrupt tissues that will not heal.

In the case of total disc replacement surgery, existing prosthetic devices have met with limited success in reproducing the biomechanics of a natural disc. Moreover, the anterior longitudinal ligament must be severed as part of the anterior approach by which the device is implanted. Worse, the severing may span two vertebral bodies for a two level reconstruction, which can lead to lessened spinal function and stability. Further, total disc replacement devices require removal of a substantial portion the disc and attachment to the adjacent vertebral bodies. The endplates of the vertebral bodies are nonuniform and typically sclerotic, which prevents the close physical joining of endplate and device surfaces required for bone ingrowth to provide adhesion and can lead to subsidence of the disc replacement device into the bone of the vertebral bodies if the endplates are shaved for contour matching. Moreover, the devices display limited motion. Specifically, as a result of the oversized implant relative to the narrow disc space, total disc replacement often results in a range of motion of only about 3.8° to 4.6°. Such a limited range of motion is the equivalent of a spinal fusion, which is defined to be motion of less than about 5°.

For example, U.S. Pat. No. 4,759,769 to Hedman et al. discloses a synthetic disc having upper and lower plates hinged together. Although the hinged disc allows forward bending between adjacent vertebrae, the hinged disc does not allow axial compression or lateral flexion. Nor does it allow axial rotation of the vertebral column at the site of the implant. Therefore, the Hedman et al. device lacks the biomechanics of a natural disc.

Likewise, the prosthetic disc device disclosed in U.S. Pat. No. 4,309,777 to Patil does not replicate natural motion between adjacent discs. The Patil device includes two cups, one of which overlaps the other and is spaced from the other by springs. The cups move only in a single axial dimension. Thus, the Patil device does not enable natural flexion of the spine in any direction. In addition, the highly constrained motion of the Patil device can lead to high device/tissue interface stresses and implant loosening.

In the case of nucleus replacement devices, historically these devices required perforation or partial excision of the annulus to insert the device. Breaking the continuity of the annular ring precludes normal stress loading of the annulus, which may be necessary for later healing. Further, degeneration of the annulus, exacerbated by damage done during implantation, may also result in increased loads placed upon the implant. Increased loads of this nature may lead to subsidence of the device into the vertebral body, device extrusion through the annular defect, or expulsion from the nuclear space. Moreover, these problems are exacerbated in the situation in which more than one disc is to be replaced because any or all of the devices may develop these problems. These problems are particularly challenging in the lumbar spine, where the discs are most highly stressed due to high bearing requirements.

A remarkable intervertebral synthetic prosthetic device that greatly reduces the problems associated with total disc replacement and conventional nucleus replacement devices is disclosed in U.S. Pat. No. 5,827,328 ("the '328 patent") to Buttermann. The Buttermann devices excise the nucleus pulposus while maintaining the biomechanical functionality of the intact annulus fibrosis. Moreover, the intervertebral prosthetic device permits at least four degrees of relative motion between two vertebral bodies on either side of targeted intervertebral disc. These degrees of relative motion include sagittal bending, coronal bending, axial rotation, and axial compression. Moreover, the compressible member permits small increments of translational movement between the vertebral bodies (i.e., fifth and sixth degrees of relative motion, namely anterior-posterior translation and side-to-side, or lateral, translation).

FIG. 1 shows an embodiment of an intervertebral prosthetic device 10 according to one embodiment of the '328 patent that is designed to replace a damaged natural disc. This device 10 is implanted by making holes in two adjacent vertebral bodies and boring through the nucleus pulposus of the intervertebral disc between the vertebral bodies. The intervertebral prosthetic device 10 has a first fixation member 14, a second fixation member 16, and a compressible member 18 that is positioned between the first fixation member 14 and the second fixation member 16. In addition to restoring the disc height, the compressible member 18 acts as a shock absorber to minimize impact loading and, thus, minimize device failure or vertebral fracture.

The first fixation member 14 is positioned in a first vertebral body 20. The second fixation member 16 is positioned within a second vertebral body 22 adjacent the first vertebral body 20. Each fixation member 14, 16 has an adjustable member 28, 30, respectively, and a support member 32, 34, respectively. Controlling the height of the adjustable members 28 and 30, along with selecting an appropriately sized support member, controls the "disc" height. The disc height is defined as the axial distance between the vertebrae above and below the operative disc.

The adjustable member 28 of the first fixation member 14 has an imaginary first longitudinal axis (shown by double-arrowed line A-A in FIG. 1) and adjustment elements 24 that allow adjustment of the height of the adjustable member 28 substantially along its longitudinal axis. In the embodiment shown in FIG. 1, the second fixation member 16 is structurally similar to the first fixation member 14, but inverted. The adjustable member 30 of the second fixation member 16 has a second longitudinal axis (shown by double-arrowed line B-B) and adjustment elements 26 that allow adjustment of the height of the adjustable member 30 substantially along its longitudinal axis.

FIG. 4 shows one embodiment of the first fixation member 14. In the embodiment shown in FIG. 1, the second fixation member 16 is structurally similar to the first fixation member 14, but inverted. Thus, the following discussion also applies to the second fixation member 16.

The adjustable member 28 of the first fixation member 14 is adjustable in an axial direction by adjustment elements 24. The adjustment elements 24 comprise telescopic struts extending between a first, outer plate 31 and a second, inner plate 33. The outer plate 31 is farther from the operative intervertebral disc and hence farther from the compressible member 18. In contrast, the inner plate 33 is closer to the operative intervertebral disc area and hence closer to the compressible member 18. In the embodiment illustrated in FIG. 1, the outer plate 31 has a bone-contacting surface 27, and the inner plate 33 has a surface 35 for positioning against the support member 32.

The adjustment elements 24 adjust the distance between the first bone-contacting plate 31 and the second plate 33, thus adjusting the height of the adjustable member 28. A surgeon may adjust the telescopic struts to increase the height of the adjustable member and thus mechanically pre-load the compressible member 18 to reproduce the axial compression absorbed by a nucleus pulposus of a natural disc. Pre-loading the compressible member restores the intervertebral height at the operative joint, restores the function of the annulus fibrosis. Pre-loading also assures close apposition of an ingrowth surface 27, 29 of the device to bone 36, 38.

Each telescopic strut is provided with a lock screw 63 to adjust the length of the strut 24 and hence control the height of the adjustable member. The lock screw 63 may comprise, for example, a pin (not shown) that extends through both the telescoping portion 65 and the housing portion 67 of the strut 24. Each strut 24 is independently adjustable. FIG. 5 shows a top view of the second plate 33 of the adjustable member 28. The adjustment elements 24 preferably are spaced equidistant from each other to enable specific height adjustment of various regions of the adjustable member.

The first and second fixation members 14 and 16 have porous portions, such as the bone-contacting surface 27, to permit bone ingrowth. In FIG. 1, the bone-contacting surface 27 of the adjustable member 28 is positioned against the subchondral bone of an endplate 36 of the superior vertebral body 20, and the bone-contacting surface 29 of the adjustable member 30 is positioned against the subchondral bone of an endplate 38 of the inferior vertebral body 22. Alternatively, a biocompatible fabric or suitable material may be wrapped around the fixation members to enable bone ingrowth. As another alternative, a biocompatible coating may be applied to the fixation members to facilitate bone ingrowth. The prosthetic device of FIG. 1 does not require conventional mechanical attachments, such as pegs or screws, to hold the prosthesis permanently in place. The intravertebral (i.e., within a vertebral body) positioning of the fixation members 14, 16 maintains the prosthetic device 10 in stable relationship at the operative intervertebral joint. The prosthetic device, however, may include mechanical or other attachments to supplement the porous portions of the fixation members and to temporarily fix the prosthetic device in place until bone ingrowth has occurred.

To further promote bone ingrowth, the adjustment elements 24 may include fins 66 extending outward from an exterior surface of the element 24, as shown in FIG. 4. The fins 66 increase the surface area of the fixation member 14 to which bone may attach. Preferably, these fins 66 are located on the adjustment elements that are positioned on the anterior side of the adjustable member 28. The prosthetic device also may include protuberances (not shown) on the bone-contacting surface of the adjustable members to increase the surface area of the porous portion of the fixation members and, thus, encourage bone ingrowth.

FIG. 6 shows a cross-section of support member 32. The support member 32 has a first surface 72 that operably faces away from the compressible member 18 and a second surface 74 that operably faces towards the compressible member 18. The first and second surfaces 72 and 74 are oblique so that a circumferential surface 77 around the support member 32 varies in width, as shown in FIG. 4. Thus, the support member 32 is wedge-shaped. In other words, the support member 32 preferably tapers from a maximum thickness at one side 73 to a minimum thickness at an opposite side 75. Generally, the support member 32 is thicker on the side of the fixation member 14 placed anteriorly in a patient's spine to account for the spine's natural curvature.

The support members are constructed with various thicknesses and with various angled surfaces, depending upon the vertebral level of the operative intervertebral joint. An angle θ shown in FIG. 6 ranges between 3°-10°. The support members are shaped to maintain sagittal alignment. Maintaining sagittal alignment avoids nonuniform loading of the compressible member and avoids early fatigue failure of that member.

The compressible member 18, which is shown in FIG. 2, can comprise at least one spring and, in the illustrated embodiment, comprises a plurality of springs 40. The compressible member 18, which is implanted in the region of an excavated nucleus pulposus of the operative intervertebral disc, is dimensioned so that the annulus fibrosis of the natural disc is at least substantially (if not completely) maintained. As a result, the intervertebral prosthetic device restores the mechanical properties of the disc without disrupting the annulus fibrosis. Retention of the annulus fibrosis maintains stability of the intervertebral joint at the implant site. In addition, the annulus fibrosis serves as a boundary for the compressible member and, therefore, minimizes the potential for accidental dislodgment of the prosthetic device.

The compressible member 18 has a top plate 42, a bottom plate 44, and a plurality of coil springs 40 extending between the top plate 42 and the bottom plate 44. The top plate 42 has a first surface 46, which is connectable to the first fixation member 14, and a second surface 48. The bottom plate 44 also has a first surface 50, which is connectable to the second fixation member 16, and a second surface 52. The springs 40 extend between the second surfaces 48 and 52 of the top plate 42 and bottom plate 44, respectively.

When pre-loaded, the compressible member 18 can have an axial height of approximately 1.5 cm, greatest at the L45 vertebral level and slightly less at the upper lumbar vertebrae. The coil springs 40 can have non-linear stiffness so that they become stiffer at higher applied loads; the nonlinear stiffness simulates physiological intervertebral stiffness. Moreover, any spring arrangement may be used that achieves sufficient axial compressive stiffness to replicate the biomechanics of the natural disc.

The compressible member includes an imaginary longitudinal axis (shown by the dashed line C-C) and an outer periphery in a plane transverse to its longitudinal axis. A largest dimension of the compressible member's outer periphery is less than or substantially equal to the diameter of a nucleus pulposus of the natural intervertebral disc. Put another way, the annulus fibrosis of the natural disc, which is substantially (if not completely) preserved during the implantation procedure, circumscribes the compressible member 18. For example, where the compressible member comprises a plurality of springs, the outer periphery of the compressible member circumscribes the springs, and the largest dimension of that outer periphery may extend to, but does not extend beyond, the nucleus pulposus. In other embodiments, where the compressible member includes a top plate and a bottom plate, and where those plates fit within the annulus fibrosis and extend beyond the outermost portions of the springs, the outer periphery of the compressible member equals the larger of the two plate peripheries. In quantitative terms, the outer periphery of the compressible member preferably ranges between 2.0 cm to 3.0 cm, which approximates the diameter of the nucleus pulposus of a natural intervertebral disc.

FIGS. 3A-3C show three embodiments of a coil spring designed to possess non-linear stiffness. In the embodiment of FIG. 3A, the coil spring 54 has a variable, or non-uniform, cross-sectional diameter 56. FIG. 3B shows another embodiment in which a coil spring 58 has a variable pitch 60, where the pitch is defined as the distance between successive coils of the spring 58. FIG. 3C shows a third embodiment of a coil spring 62 in which at least two of the spring coils have different radii 64 measured from an imaginary axis D-D extending along the central axis of the spring 62.

A method of intervertebral disc replacement now will be described in connection with FIGS. 8-14. FIG. 8 shows a pathological intervertebral disc 90 located between a superior vertebral body 92 and an inferior vertebral body 94. Prior to implantation, a surgeon performs a partial vertebrectomy to excise bone matter from the superior vertebral body 92 for receipt of a fixation member. This procedure can be performed using a cutting guide and reamer. Bone harvested from the vertebral body 92 by the reamer can be used after implantation of the prosthetic device to promote bone ingrowth into the prosthetic device, as later described. The partial vertebrectomy creates a cavity bounded by subchondral bone of a distant endplate 96 and subchondral bone of a near endplate 98 of the superior vertebral body 92. FIG. 9 shows a cross-sectional view of the superior vertebral body 92 after the partial vertebrectomy, as taken along line 9-9 in FIG. 8.

The surgeon next excises the nucleus pulposus of the damaged disc to create a cavity 100, as shown in FIG. 10, for receipt of the compressible member. The annulus fibrosis 102, seen in FIG. 11, is maintained.

Upon completion of the partial vertebrectomies, the surgeon implants a fixation member 104 into the inferior vertebral body 94, as shown in FIG. 11. The surgeon can select a support member with an appropriate thickness to accommodate the angulation at the operative intervertebral levels. The surgeon then inserts a compressible member 106 (via the cavity formed in the superior vertebral body 92) into the cavity formerly containing the nucleus pulposus of the damaged disc and connects it to the inferior fixation member 104, as shown in FIG. 12. The compressible member 106 and the fixation member 104 may be connected by conventional attachment members, such as screws, or by biocompatible cement or a suitable adhesive composition. Finally, the surgeon implants another fixation member, similar to the one implanted in the inferior vertebral body 94, yet inverted, in the superior vertebral body 92. Connection of that fixation member to the compressible member 106 forms an intervertebral prosthetic device like the one shown in FIG. 1.

Once the fixation members are in place, the surgeon expands each adjustable member. The surgeon applies distraction until the adjustable member is seated against the subchondral bone and distant endplate 96 of the vertebral body and until the desired compression has been applied to the compressible member. The adjustment elements of the adjustable member are then secured, e.g., FIG. 13 shows rotation of the lock screws 112 of individual telescopic struts 108 to secure the struts at an appropriate height.

The surgeon next packs cancellous bone grafts 118, typically obtained during creation of the cavity in the vertebral body, around the struts of each adjustable member, as shown in FIG. 14. The growth of bone around the fixation member and into its porous surfaces secures the intervertebral prosthetic device in place, absent mechanical attachments typically used in conventional disc prostheses. The surgeon then replaces the cortical bone from the partial vertebrectomy procedure and, if needed, secures it with a bone screw, suture or bone cement. In certain clinical situations, as when there is poor bone healing or insufficient bone, the surgeon may elect to use bone cement to attach the fixation members to the vertebrae.

Although the embodiment shown in FIGS. 1-6 is effective, in some instances it may be unnecessarily invasive as a result of its implantation via two vertebral body holes. FIG. 7 shows a second, less invasive embodiment described in the '328 patent, in which a prosthetic device is implanted via one vertebral body hole.

FIG. 7 shows an intervertebral prosthetic device 76 according to this second embodiment that comprises a first fixation member 78, a second fixation member 80, and a compressible member 82. The compressible member 82 is positioned between the first and second fixation members 78, 80. The second fixation member 80 comprises a wedge-shaped support member with an upper surface 84 that attaches to the compressible member 82 and a lower surface 86 that rests upon subchondral bone of a near endplate 88 of an inferior vertebral body. In this embodiment, adjustment of the first fixation member 78 pre-loads the compressible member 82 to an appropriate extent. Also, in this embodiment, a lower surface 86 of the support member 80 may be composed of a porous material and may have a slightly convex shape to match the natural contour of the near endplate of the inferior vertebral body.

The implantation of the FIG. 7 embodiment is similar to the implantation of the FIG. 1 embodiment. Specifically, similar to the embodiment shown in FIG. 10, a cavity may be formed in the superior vertebral body 92 and then extended through the nucleus pulposus of the intervertebral disc therebelow. At this time, the compressible member with the lower fixation member 80 affixed thereto may be inserted through the cavity in the vertebral body and then pushed downward into the cavity 100 in the intervertebral disc. Subsequently, the upper fixation member 78 is: (a) positioned in the cavity formed in the superior vertebral body 92; (b) connected to the compressible member; and (c) adjusted in the manner previous discussed with respect to the FIG. 1 embodiment. Of course, the cavity in the superior vertebral body 92 is then closed also in the manner previously described.

As evident from the embodiments of FIGS. 1 and 7, the intervertebral prosthetic device embodiments have a modular design so that the prosthesis may be sized to the patient's anatomy and designed for the patient's condition. The modular design also enables replacement of individual components of the prosthesis (i.e., a fixation member or a compressible member), rather than replacement of the entire prosthesis should one component fail. As a result, the compressible member can be attached to the fixation members by mechanical attachments, such as screws, rather than bone cement so that a surgeon may easily replace damaged or worn components.

Unfortunately, the embodiment shown in FIG. 1 precludes use when reconstructing multiple adjacent discs. Additionally, although the less invasive embodiment shown in FIG. 7 may be implanted via only one vertebral body hole, it may be less effective than the embodiment shown in FIG. 1 when used in patients with low bone density. Specifically, the FIG. 7 may be less effective as a result of inability to adequately fix the lower fixation member 80 to the vertebral body below the compressible member. Further, this inability to adequate fix the lower fixation member 80 may, in turn, lead to subsidence of the device into the vertebral body adjacent the lower fixation member 80.

SUMMARY

An embodiment of the invention addresses a prosthetic device that includes: a first compressible member sized to substantially replace the nucleus pulposus of a first intervertebral disc; a second compressible member sized to substantially replace the nucleus pulposus of a second intervertebral disc that is separated from the first intervertebral disc by a vertebral body; and a fixation member sized to fit within a cavity in the vertebral body between the first and second compressible members.

Another embodiment of the invention addresses a prosthetic device that includes: a fixation member sized to fit within a cavity in a first vertebral body; and a compressible member sized to substantially replace a nucleus pulposus of an intervertebral disc adjacent the vertebral body. A first side of the compressible member is configured to engage the fixation member and a second side of the compressible member is configured to engage a second vertebral body. The second side of the compressible member is configured to fit within a seat formed in the cortical bone of the endplate of the second vertebral body.

Another embodiment of the invention addresses an intervertebral prosthetic device for implantation in a spine that includes: (a) a rigid fixation member having a fixed length, the rigid fixation member being configured to be placed in a cavity of a vertebral body and against bone of the vertebral body; and (b) a first compressible member configured to be placed in a cavity in a first intervertebral disc adjacent the vertebral body and to be secured to the rigid fixation member. The compressible member is constructed to remain compressible after implantation and has at least one compressible element that remains compressible after implantation. The rigid fixation member is sized to compress the compressible member a predetermined amount when the rigid fixation member and the first compressible member are placed in the cavity in the first vertebral body and in the cavity in the first intervertebral disc, respectively.

Another embodiment of the invention addresses an intervertebral prosthetic device for implantation in a spine. This device includes: (a) a fixation member configured to be placed in a cavity of a vertebral body, the fixation member including: (i) an outer member configured to be placed against bone of the vertebral body; (ii) an inner member opposite the outer member; and (iii) at least one adjustment element that extends between the outer and inner members and that is configured to adjust a length dimension of the fixation member along its longitudinal axis; (b) a compressible member configured to be placed in a cavity in an intervertebral disc adjacent the vertebral body and configured to be secured to the inner member of the fixation member; and (c) a spacer sized to fit between the outer and inner members of the fixation member to maintain the fixation member at a desired length dimension.

Another embodiment of the invention addresses an intervertebral prosthetic device for implantation in a spine. This device includes: (a) a fixation member configured to be placed in a cavity of a vertebral body, the fixation member including: (i) an outer member configured to be placed against bone of the vertebral body; (ii) an inner member opposite the outer member; and (iii) a longitudinal axis extending between the outer and inner members; and (b) a compressible member configured to be placed in a cavity in an intervertebral disc and to be secured to the inner member of the fixation member. The compressible member is constructed to remain compressible after implantation. The outer member includes a tab extending outward along an axis different from the longitudinal axis.

Another embodiment of the invention addresses an intervertebral prosthetic device for implantation in a spine. This device includes: (a) a fixation member configured to be placed in a cavity of a vertebral body, the fixation member including: (i) an outer member configured to be placed against bone of the vertebral body; (ii) an inner member opposite the outer member; and (iii) a longitudinal axis extending between the outer and inner members; (b) a compressible member configured to be placed in a cavity in an intervertebral disc adjacent the vertebral body and to configured be secured to the fixation member; and (c) at least one anchor element configured to immobilize and/or stabilize the compressible member and/or the fixation member.

Another embodiment of the invention addresses a prosthetic device that includes: (a) a fixation member sized to fit within a cavity in a first vertebral body; and (b) a compressible member that includes: (i) a cup-shaped base member; (ii) an upper member; and (iii) one or more compressible elements provided between the base member and the upper member. The compressible member is sized to substantially replace a nucleus pulposus of an intervertebral disc adjacent the vertebral body.

Another embodiment of the invention addresses a prosthetic device that includes: (a) a fixation member sized to fit within a cavity in a first vertebral body; and (b) a compressible member that includes: (i) a base member; (ii) an upper member that includes a spike; and (iii) one or more compressible elements provided between the base member and the upper member. The one or more compressible elements are sized to substantially replace a nucleus pulposus of an intervertebral disc adjacent the vertebral body.

Another embodiment of the invention addresses a prosthetic device that includes: (a) a fixation member sized to fit within a cavity in a first vertebral body; and (b) a compressible member that includes: (i) a base member; (ii) an upper member comprising a ball-and-socket joint; and (iii) one or more compressible elements provided between the base member and the upper member. The compressible member is sized to substantially replace a nucleus pulposus of an intervertebral disc adjacent the vertebral body.

Another embodiment of the invention addresses a prosthetic device that includes: (a) a fixation member sized to fit within a cavity in a first vertebral body; and (b) a compressible member that includes: (i) a base member; (ii) an upper member; and (iii) one or more compressible elements provided between the base member and the upper member. The compressible member is sized to substantially replace a nucleus pulposus of an intervertebral disc adjacent the vertebral body. The base member is adjustable in a radial direction.

Another embodiment of the invention addresses a method of spinal prosthetic implantation. This method includes: (a) creating a cavity in a first vertebral body; (b) cutting a first hole through either a lower or an upper endplate of the vertebral body and through the nucleus pulposus of a first intervertebral disc adjacent thereto, thereby creating a first opening in the first intervertebral disc; (c) cutting a second hole through the other of the lower and upper endplate of the vertebral body and through the nucleus pulposus of a second intervertebral disc adjacent thereto, thereby creating a second opening in the second intervertebral disc; (d) implanting a first compressible member into one of the first and second openings; (e) implanting a second compressible member into the other of the first or second openings; and (f) implanting a fixation member into the cavity in the first vertebral body.

Another embodiment of the invention addresses a method of spinal prosthetic implantation. This method includes: (a) creating a cavity in a first vertebral body; (b) cutting through an endplate of the vertebral body and through the nucleus pulposus of an adjacent intervertebral disc, thereby creating an opening in the intervertebral disc; (c) cutting into the cortical bone of a second vertebral body on the other side of the intervertebral disc to create a seat; (d) implanting a compressible member into the opening in the intervertebral disc such that a distal end of the compressible member sits within the seat in the second vertebral body; and (e) implanting a fixation member in the cavity in the first vertebral body.

Another embodiment of the invention addresses a method of spinal prosthetic implantation. This method includes: (a) creating a cavity in a vertebral body; (b) cutting a hole through either a lower or an upper endplate of the vertebral body and through the nucleus pulposus of an intervertebral disc adjacent thereto, thereby creating an opening in the intervertebral disc; (c) implanting a compressible member into the opening in the intervertebral disc; and (d) implanting a fixation member into the cavity in the first vertebral body. The compressible member comprises a base member that is wider than the hole cut in the vertebral body through which the first compressible member is implanted. The step of implanting the compressible member into the opening includes: (i) maneuvering the base member of the compressible member so that it passes through the hole and into the opening; and (ii) rotating the base member so that it substantially covers the hole.

Another embodiment of the invention addresses a method of spinal prosthetic implantation. This method includes: (a) creating a cavity in a vertebral body; (b) cutting a hole through either a lower or an upper endplate of the vertebral body and through the nucleus pulposus of an intervertebral disc adjacent thereto, thereby creating an opening in the intervertebral disc; (c) implanting a compressible member into the opening in the intervertebral disc; and (d) implanting a fixation member into the cavity in the first vertebral body. The compressible member comprises a base member that is radially adjustable to be wider than the hole cut in the vertebral body through which the compressible member is implanted. The step of implanting the compressible member into the opening includes: (i) maneuvering the base member of the compressible member so that it passes through the hole and into the opening; and (ii) radially adjusting the base member so that it substantially covers the hole.

Another embodiment of the invention addresses a drill guide for use in spinal surgery. The drill guide includes a body having a first leg and a second leg. The first leg is dimensioned to be fixed relative to an intervertebral prosthetic member mounted in a cavity of a first vertebral body. The second leg is dimensioned to extend from the first leg, adjacent the first vertebral body, to a free end, adjacent at least one of an intervertebral disc and a second vertebral body. The second leg includes at least one drilling channel extending through the second leg and the free end of the second leg comprises a drill positioning block through which the at least one drilling channel extends.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 15A is a top perspective view of an intervertebral prosthetic device and a drill guide used to drill holes in the intervertebral bone in accordance with the invention; FIGS. 15B-15D are a first side elevation view, a second side elevation view, and a top plan view, respectively, of the intervertebral prosthetic device and the drill guide of FIG. 15A.

FIG. 17A is a top perspective view of the intervertebral prosthetic device and the drill guide of FIG. 15A, showing placement of anchor elements through the drill guide and a compressible member of the intervertebral prosthetic device; FIGS. 17B-17D are a first side elevation view, a second side elevation view, and a top plan view, respectively, of the intervertebral prosthetic device, including the anchor elements, and the drill guide of FIG. 17A.

FIG. 18A is a side elevation view of an intervertebral prosthetic device, including anchor elements, and a drill guide in accordance with another embodiment of the invention; FIGS. 18B-18D are a top perspective view, a side elevation view, and a top plan view, respectively, of the intervertebral prosthetic device, including the anchor elements, and the drill guide of FIG. 18A.

FIGS. 19A-19E are a top perspective view, a bottom plan view, a bottom perspective view, a first side elevation view, and a second side elevation view, respectively, of a plate of an embodiment of a fixation member in accordance with the invention.

FIG. 21A is a top perspective view of an intervertebral prosthetic device, including anchor elements and spacers, in accordance with another embodiment of the invention; FIGS. 21B-21D are a first side elevation view, a second side elevation view, and a top plan view, respectively, of the intervertebral prosthetic device, including the anchor elements and the spacers, of FIG. 21A.

FIG. 22A is a top perspective view of an intervertebral prosthetic device, including spacers, in accordance with another embodiment of the invention; FIGS. 22B-22D are a first side elevation view, a second side elevation view, and a top plan view, respectively, of the intervertebral prosthetic device, including the spacers, of FIG. 21A.

FIGS. 30A and 30B are cross-sectional views of another alternate embodiment compressible member in which FIG. 30A shows the compressible member partial implanted and FIG. 30B shows the compressible member completely implanted.

FIG. 32 is a cross-sectional view of alternate embodiment compressible member implanted in an intervertebral disc.

FIG. 34A is a side elevation view of a compressor that includes a pair of endplate and nucleus cutters and FIG. 34B is a side elevation view of a distractor that includes an endplate and nucleus cutter.

DETAILED DESCRIPTION

Figure 7:
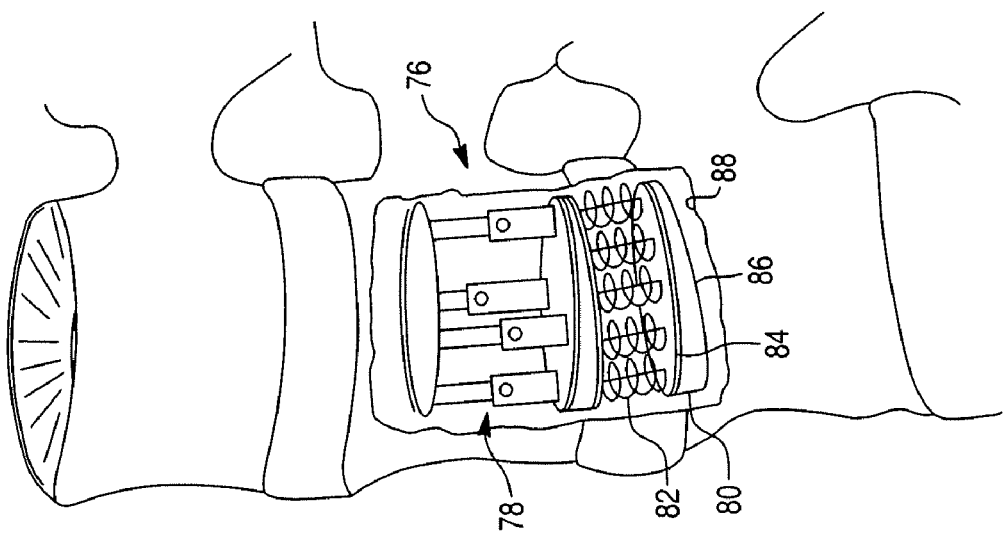
FIG. 7 is a schematic, cut-away side view of another prior art intervertebral prosthetic device implanted in a spine.
Figure 1:
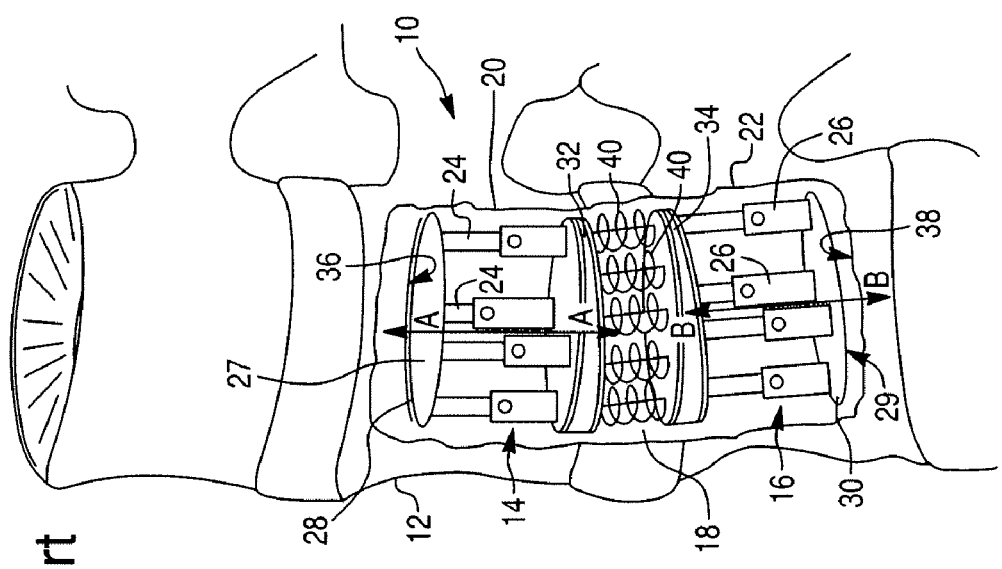
FIG. 1 is a schematic, cut-away side view of a prior art intervertebral prosthetic device implanted in a spine.
Figure 2:
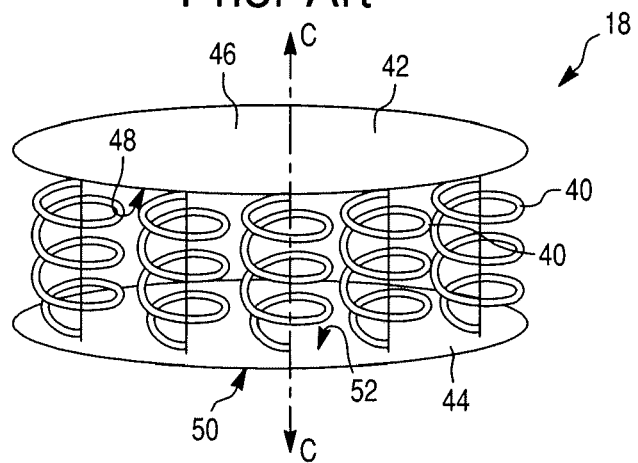
FIG. 2 is a top perspective view of a compressible member of the intervertebral prosthetic device of FIG. 1.
Figure 3A:
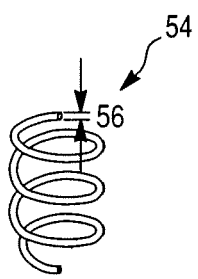
FIGS. 3A-3C are top perspective views of different embodiments of a spring of the compressible member shown in FIG. 1.
Figure 3B:
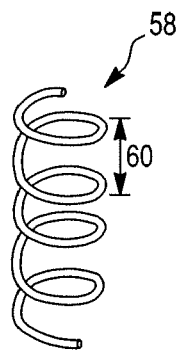
Figure 3C:
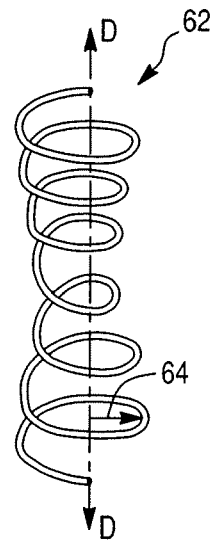
Figure 5:
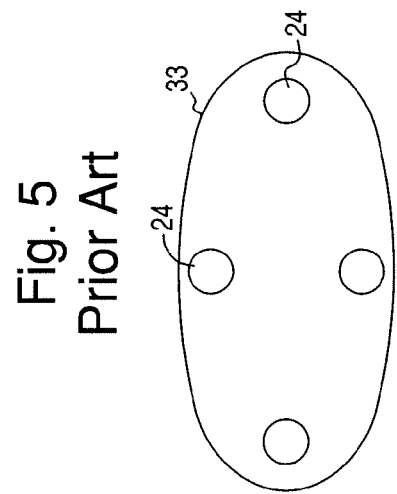
FIG. 5 is a top view of a plate of the adjustable member shown in FIG. 1.

Although the less invasive embodiment shown in FIG. 7 may not be as effective as the embodiment shown in FIG. 1 and/or may be subject to subsidence, the ability to implant a disc replacement prosthetic device via a hole formed in only one adjacent vertebral body is minimally invasive and is, therefore, advantageous. As a result, the question becomes: how can one replace one or more discs via one vertebral body hole while: (a) greatly reducing the likelihood of subsidence, (b) making the device adaptable to particular patients and/or to the particular disc being replaced; (c) ensuring that the device remains in proper position; (d) providing a straightforward method of implantation; (e) making it cost effective for the patient.

The answer to one or more of the parts to this question lies in the prosthetic device embodiments disclosed herein. These prosthetic device embodiments are not only readily implantable via a hole in a single vertebral body, they are so implantable while: (a) reducing the likelihood subsidence by means of anchors and tabs which serve to fix the device to the cortical bone of the vertebral body; (b) being adaptable by means of various compressible member embodiments; (c) ensuring the device remains in position by being fixedly engaged with the vertebrae and by being encapsulated by the annulus fibrosis; (d) being implantable in a time frame which is no longer than current implantation surgery; and (e) being cost effective by means of being modular and adjustable. The various embodiments of this novel prosthetic device will now be described with reference to the drawings, wherein like numerals indicate like parts.

A prosthetic device 200 that minimizes the likelihood that the device may subside in patients with osteopenic bone is shown in FIGS. 15A-15D and 17A-17D. In certain patients having thin bones, the bone (labeled 36, 38 in FIG. 1, and labeled 88 in FIG. 7) in areas adjacent the implanted prosthetic device may be subject to being crushed and/or collapse under heavy loads. This condition also may occur in other patients after implantation of the prosthetic device, but before the bone graft has time to heal. To minimize subsidence, one or more anchor elements, such as pins, rods, or screws, can be threaded either through a fixation member or through the compressible member to fix the prosthetic device in the hard outer cortical bone of the vertebra in which the cavity was created for device implantation.

The following description of FIGS. 15A-15D and 17A-17D relates to a prosthetic device embodiment having a compressible member and only one fixation member. However, it should be understood that the features described below can be applied to a prosthetic device having a fixation member on either side of the compressible member (as shown in FIGS. 21A-21D) or to a prosthetic device having two compressible members on either side of a fixation member (as shown in FIGS. 25-28).

The one compressible member/one fixation member embodiment of FIGS. 15A-15D, 17A-17D is similar to the embodiment of FIG. 7. However, whereas the FIG. 7 embodiment provides for a separate second fixation member, the embodiment of FIGS. 15A-15D, 17A-17D incorporates at least some of the functionality of the second fixation member into the compressible member, amongst other improvements as later described in detail.

FIGS. 15A-15D and 17A-17D show a prosthetic device 200 having a fixation member 214 for fixation within a cavity of a first vertebral body, and a compressible member 218 for implantation in the region of an excavated nucleus pulposus of an operative intervertebral disc. In this embodiment, the fixation member 214 comprises an adjustable member having an outer plate 250 and an inner plate 252. The compressible member 218 includes a first plate 242, a second plate 244, and one or more compressible elements. In the embodiment shown, the compressible elements are a plurality of coil springs 240, positioned between the plates 242, 244. Adjacent plates of the adjustable fixation member 214 and the compressible member 218 can be secured directly together. That is, an inner plate 252 of the fixation member 214 can include an angled protrusion 253 that mates with an angled recess 243 in the first plate 242 of the compressible member 218 in the manner of a dovetail joint's tendon and mortise. The angled portions 253, 243 secure the fixation member 214 and the compressible member 218 together in a keyed fit, without need for other fasteners or fastening materials. It will be understood that, in an alternative embodiment, the angled protrusion can be formed on the first plate of the compressible member, and the angled recess can be formed in the inner plate of the fixation member.

As previously mentioned, the prosthetic device 200 is designed to minimize subsidence of the device 200 into bone adjacent the device 200 by employing anchor elements to secure the device 200 into hard outer cortical bone. In the illustrated embodiment, plate 244 of the compressible member 218 includes holes 246 for receipt of anchor elements 310. A drill guide can be used to create holes through the cortical bone toward the holes 246 in the device 200. FIGS. 16A-16D show an embodiment of the drill guide 300. The drill guide 300 includes an L-shaped body 302 having a curved face 304 at one end and a drill positioning block 306 at the other end. The drill positioning block 306 can have one or more drilling channels 308. The drilling channels 308 are configured to guide a drill bit through the bone toward the holes 246 in the plate 244 of the compressible member 218.

As best seen in FIG. 15A, the drill guide 300 can temporarily engage prosthetic device 200 to guide the drilling of holes through bone toward holes 246 in prosthetic device 200. The guide 300 subsequently facilitates placement of the anchor elements 310 through the holes 246, as best seen in FIG. 17A. To properly position the drill guide 300 relative to prosthetic device 200, an upper portion 301 of the L-shaped body 302 is pushed between two adjustment elements 224 of the fixation member 214 such that the curved face 304 aligns with and engages a third adjustment element 224 of fixation member 214, as shown in FIG. 15A. As the upper portion 301 of the L-shaped body 302 has a width 303 which is substantially equal to the distance between the two adjustment elements 224 through which it is pushed, when the curved face 304 meets the third adjustment elements 224, the three adjustment elements 224 substantially immobilize the drill guide 300 with respect to the device 200.

Other embodiments of the drill guide need not include curved face 304 and can be configured to mount to other portions of the prosthetic device. In addition, the L-shaped body of the drill guide 300 can be configured to be adjustable along each of the two legs that form the "L". For example, each leg of the "L" can comprise telescoping elements to lengthen or shorten the leg, depending on the size of the prosthetic device and the position of holes 246 of the compressible member 218. Further, as an alternative to mounting the drill guide 300 to the prosthetic device 200, the guide 300 can be mounted to the outer vertebral body set to receive fixation member 214. In addition, where it is inconvenient or undesirable to use a drill guide 300, another technique, such as fluoroscopic imaging, may be used to determine drill placement. However, such a protocol may be less accurate.

Once holes have been made in the bone, anchor elements 310 can be inserted through drilling channels 308, through the newly-drilled holes in the bone, and through the holes 246 in the compressible member 218, as shown in FIGS. 17A-17D. The drill guide 300 then can be removed from the prosthetic device 200.

The anchor elements 310 can comprises rods, screws, or any other suitable support structure. In addition, the anchor elements 310 themselves can include small holes or irregularities on their surface, or they may have a bioreactive coating such as hydroxyapatite, to enhance fixation to the bone so that the anchor elements 310 do not back out of holes 246.

Although the figures show the anchor elements 310 arranged parallel to each other, holes 246 can be arranged so that the anchor elements 310 diverge or converge. Appropriate holes can be drilled through the cortical bone by reconfiguring drilling channels 308 in the drill positioning block 306 to align with the converging/diverging holes in the prosthetic device. Alternatively, the drill guide 300 may be repositioned after drilling a first hole through the bone that is aligned with a first hole in the prosthetic device, and before drilling a second hole that is aligned with a second hole in the prosthetic device.

In the embodiment of FIGS. 17A-17D, the anchor elements 310 are dimensioned to traverse the entire diameter of the vertebral body to obtain bi-cortical purchase, that is, fixation in the hard outer cortical bone on either side of the vertebral body. Alternatively, the anchor elements 310 can be shortened so that they to traverse only part of the diameter of the vertebral body to obtain uni-cortical purchase, that is, fixation in the hard outer cortical bone on only one side of the vertebral body.

Further, although the anchor elements 310 are shown passing through the bottom plate 244 of the compressible member 218, in alternative embodiments, the site for placement of the anchor elements 310 can be through either plate 250, 252 of the fixation member 214 or through the upper plate 242 of the compressible member 218. Moreover, as shown in FIGS. 18A-18D, rather than passing through a portion of the prosthetic device, the anchor elements 310 can pass under and adjacent the lowermost plate of the prosthetic device to minimize subsidence of the device into the cancellous subchondral bone in the central portion of the vertebral body.

More specifically, FIGS. 18A-18D show an embodiment of a prosthetic device 400 having a fixation member 414 and a compressible member 418. The compressible member 418 has a bottom plate 444, here shown with a convex lowermost surface 445. The convex lowermost surface 445 may be configured to sit within a correspondingly shaped concave seat 2050 (shown in FIG. 24) formed in the cortical bone of an endplate of an adjacent vertebral body. The anchor elements 310 are positioned under and just adjacent to this lowermost surface 445 to minimize subsidence of the prosthetic device 400.

Figure 20:
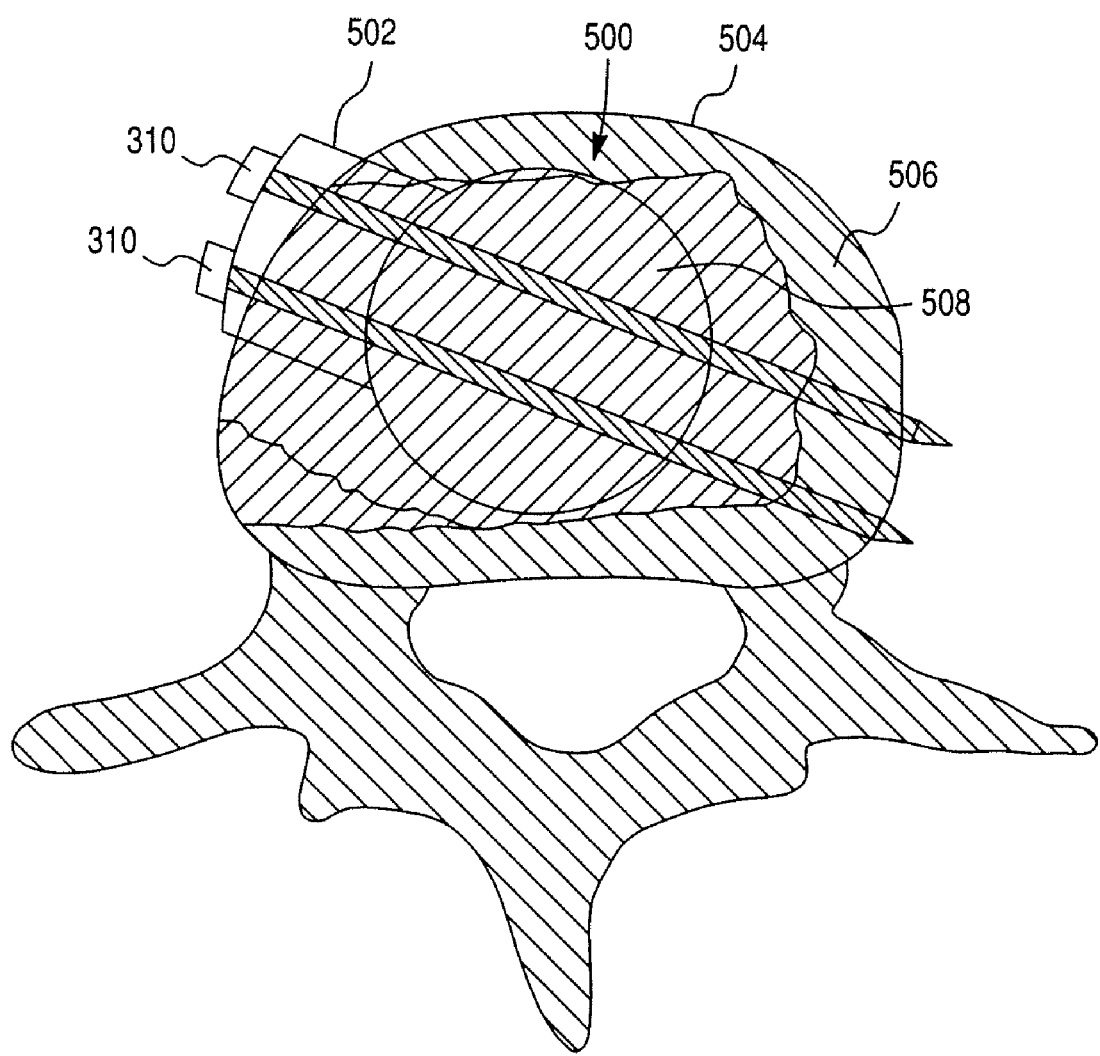
FIG. 20 is a sectional view of a vertebra, including a plate, as shown in FIGS. 19A-19E, implanted in the vertebra.
Figure 23A:
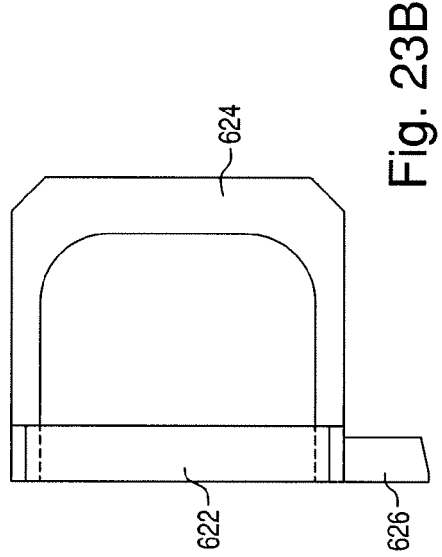
FIGS. 23A-23D are a top perspective view, a first side elevation view, a second side elevation view, and a top plan view, respectively, of a spacer.
Figure 23B:
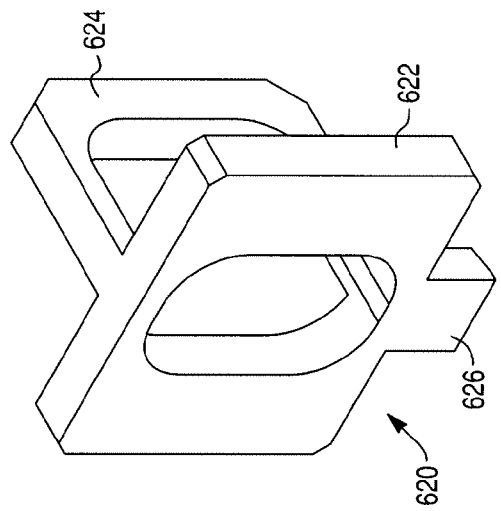
Figure 23C:
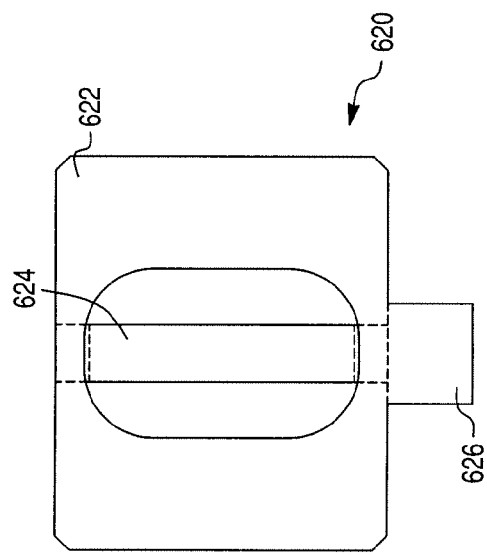
Figure 23D:
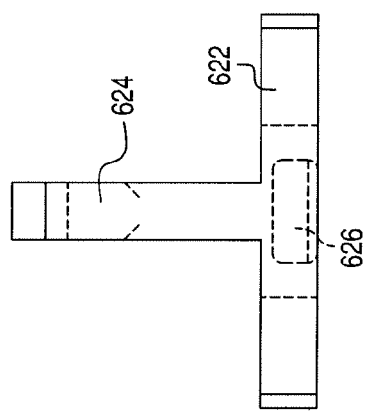

In yet another aspect of the present invention, either or both of the plates of the fixation member can include a tab to help minimize subsidence of the prosthetic device. FIGS. 19A-19E show a plate 500 for a fixation member that includes a tab 502 extending from the periphery of the generally circular, main portion of the plate 500. The tab 502 is configured to rest on outer cortical bone of a vertebral body. In this regard, FIG. 20 is a sectional view through a vertebral body, illustrating a plate 500 with a tab 502 extending into outer cortical bone 506 of the vertebral body 504. The tab 502 inhibits the ability of the prosthetic device to sink into the cancellous bone 508 of the vertebral body 504.

The plate 500 may also include a riser 510 through which holes 511, which are configured to receive anchor elements 310, can extend. In addition, a drill bit can be guided through the holes 511 in the riser 510 to drill holes through the bone of the vertebral body, thereby eliminating the need for drill guide 300. Although plate 500 is shown in FIGS. 19A-19E and 22 with both a tab 502 and a riser 510 with holes 511 for anchor elements 310, it will be understood that other embodiments of the plate can include only a tab, such as in FIG. 22A, or can include holes to receive anchor elements 310 but lack a tab.

Another prosthetic device embodiment 700 that incorporates fixation plates like fixation plate 500 in embodiment shown in FIGS. 19A-19E is shown in FIGS. 21A-21D. This prosthetic device 700 has first and second fixation members 714, 716 and a compressible member 818. The fixation members 714, 716 each include a fixation plate 750 on their outer ends; the plates 750 have tabs 751 extending therefrom. When the prosthetic device 700 is implanted in upper and lower vertebral bodies, the tabs 751 rest on the outer cortical bone of the vertebral bodies. Anchor elements 310 may extend through the cortical bone of the vertebral bodies and through holes 713 formed in the tabs 751, to enhance the stability of the prosthetic device 700.

Figure 4:
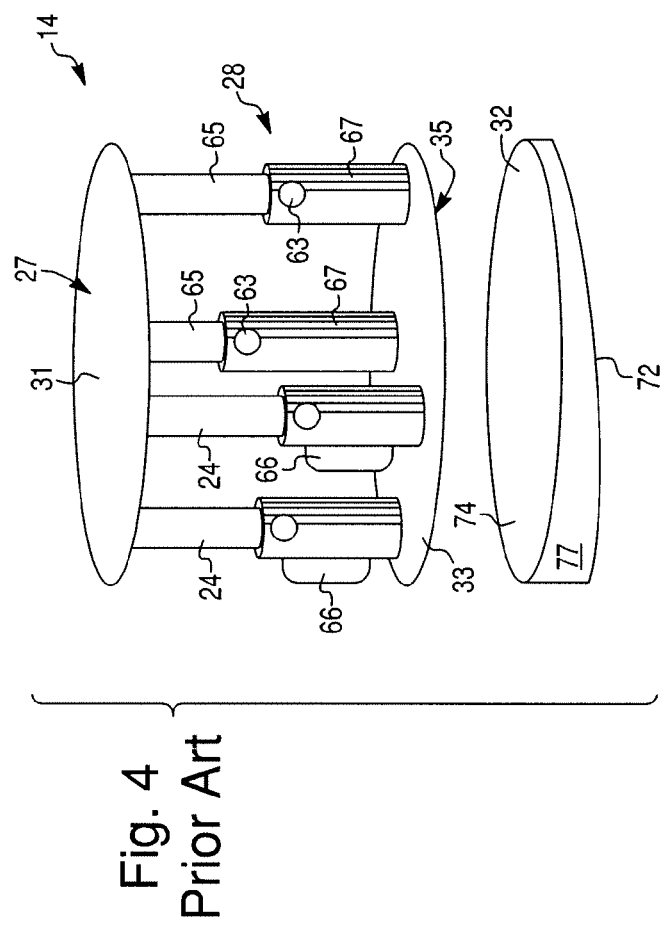
FIG. 4 is a top perspective, partially exploded view of a fixation member of the intervertebral prosthetic device of FIG. 1 and shows an adjustable member and a support member.
Figure 6:
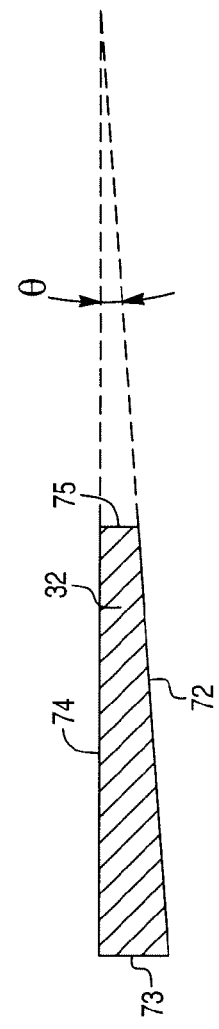
FIG. 6 is a side view, in cross-section, of the support member shown in FIG. 1.
Figure 8:
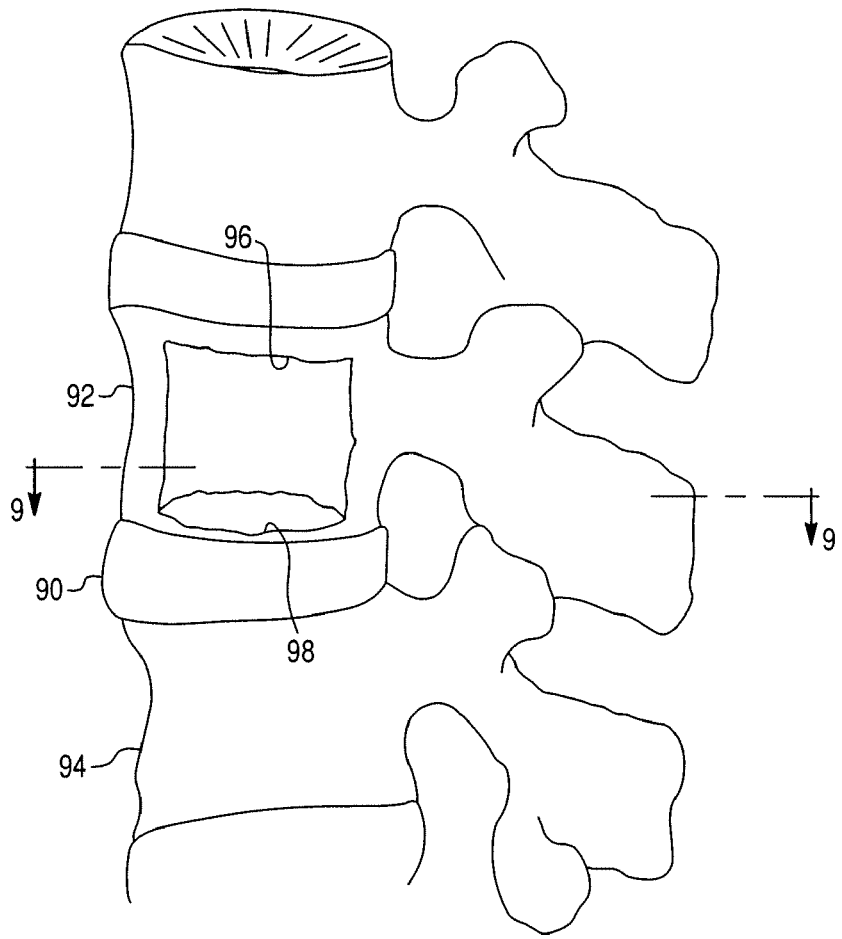
FIG. 8 is a schematic, cut-away side view showing subchondral bones of a superior vertebral body after a partial vertebrectomy.
Figure 9:
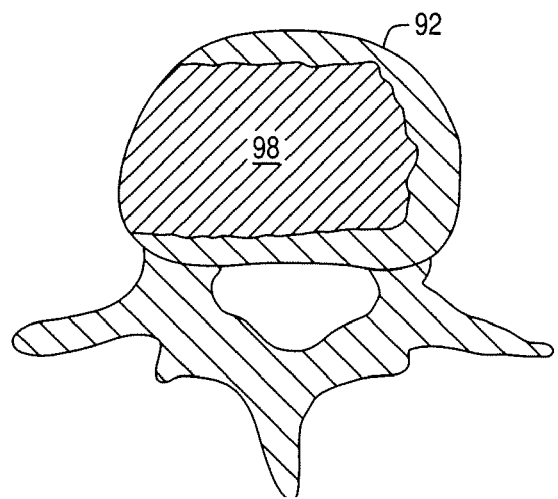
FIG. 9 is a sectional view of a vertebra after creating a cavity within the vertebral body, as taken along line 9-9 of FIG. 8.
Figure 10:
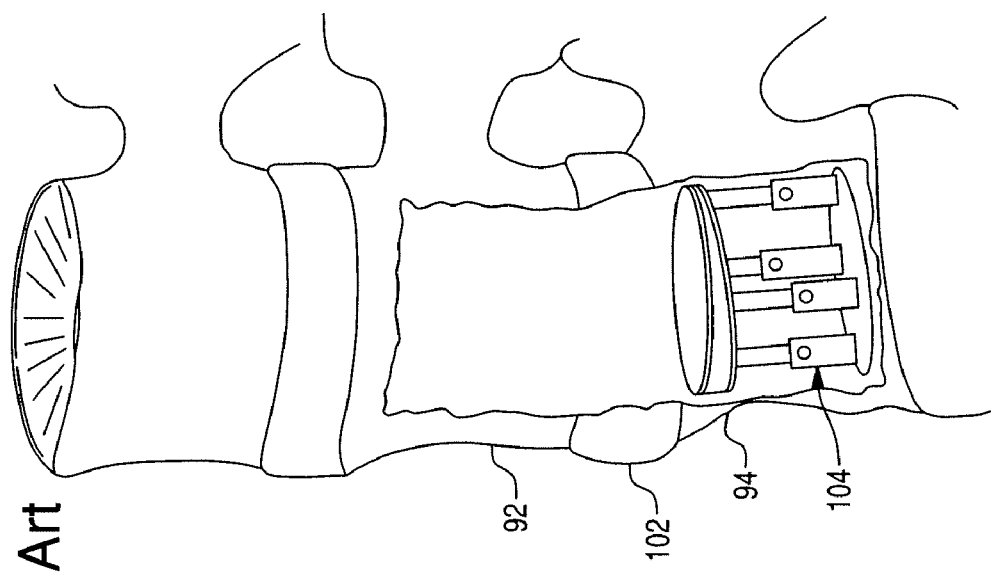
FIG. 10 is a schematic, cut-away side view of a vertebral joint area after creating a cavity within the vertebral body and excision of a nucleus pulposus of a natural disc.
Figure 11:
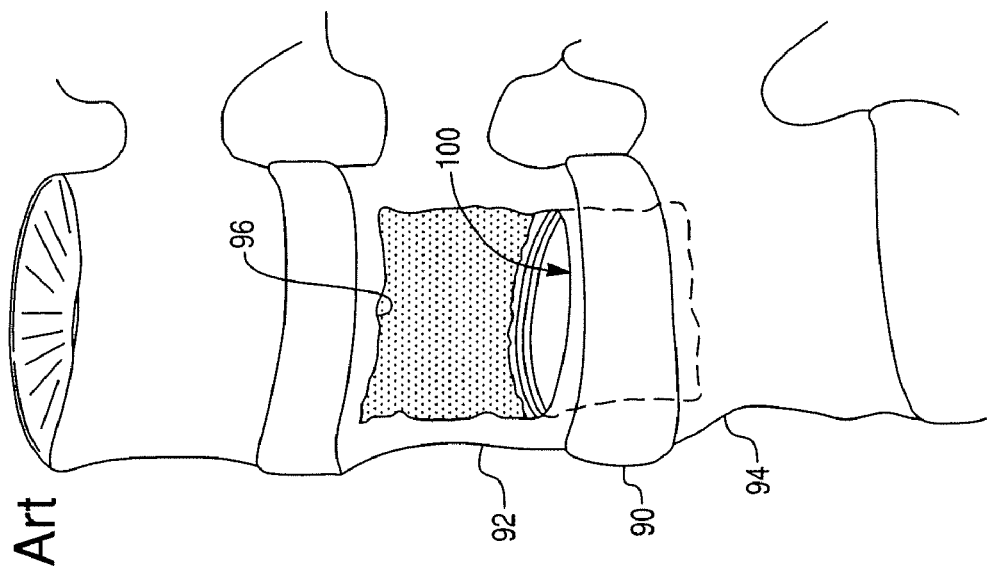
FIG. 11 is a schematic, cut-away side view of a vertebral joint and shows a fixation member, including an adjustable member and a support member, implanted in an inferior vertebral body.
Figure 12:
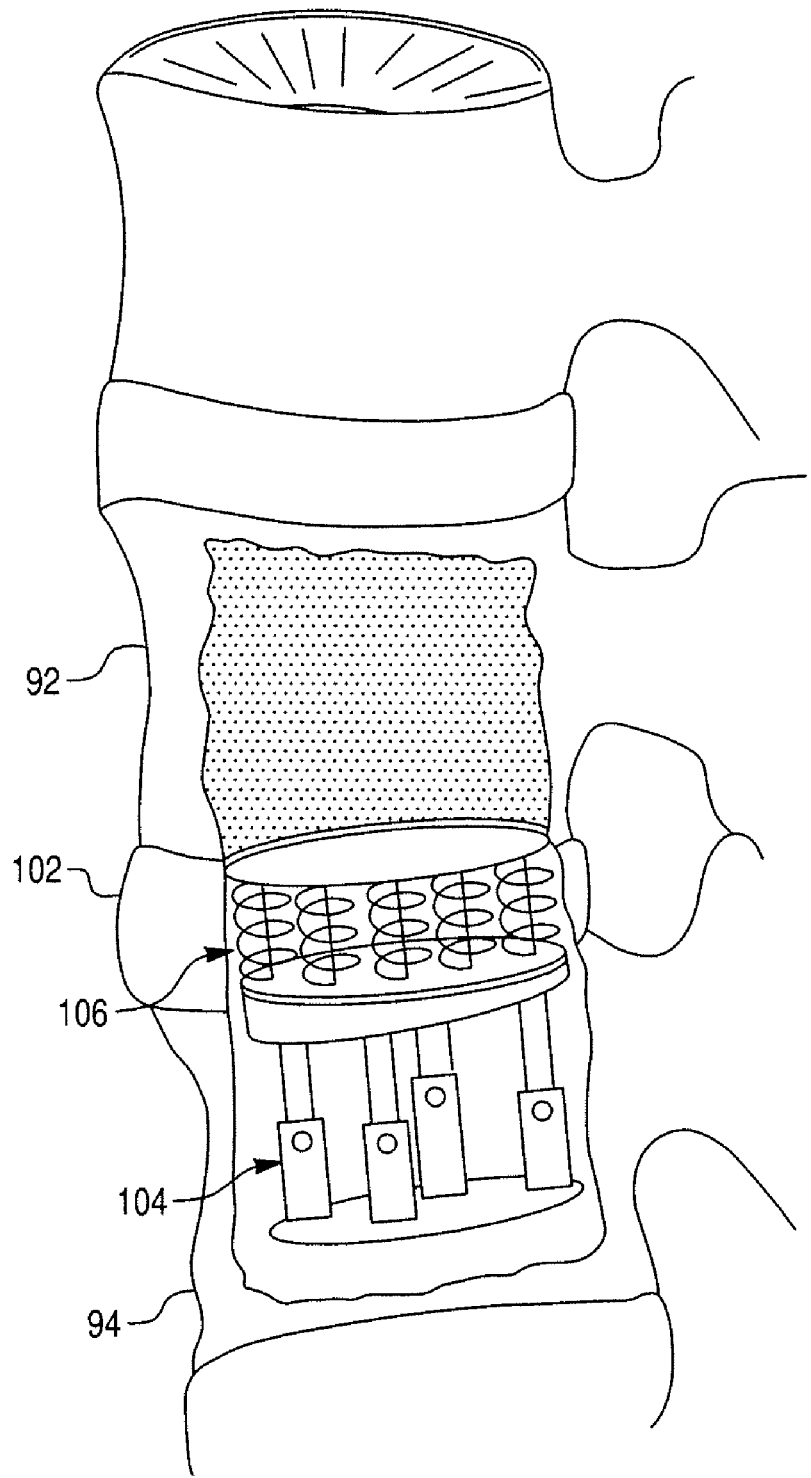
FIG. 12 is a schematic, cut-away side view of a vertebral joint and shows a compressible member implanted in an intervertebral joint.
Figure 14:
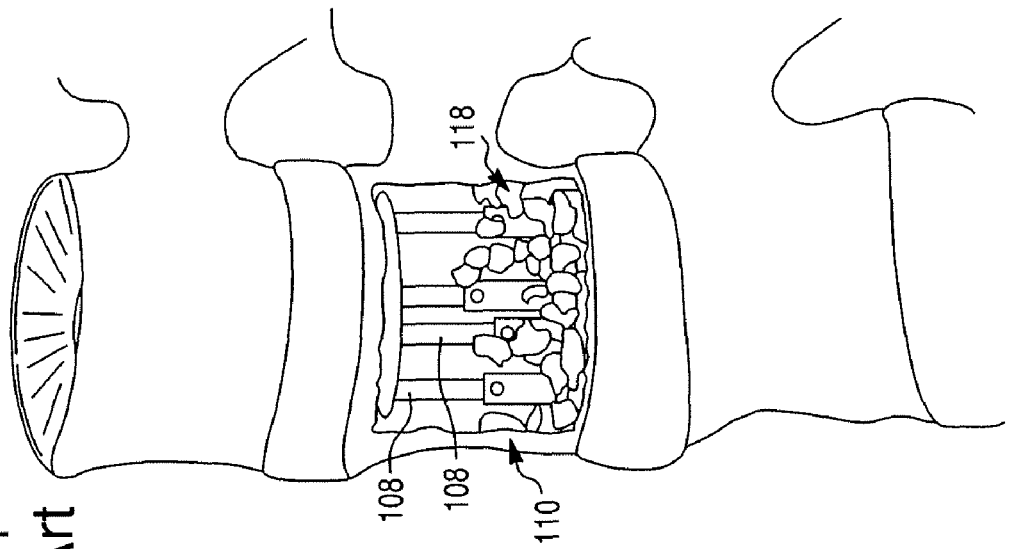
FIG. 14 is a schematic, cut-away side view of a vertebral joint and shows a technique for bone grafting an adjustable member in a superior vertebral body.
Figure 13:
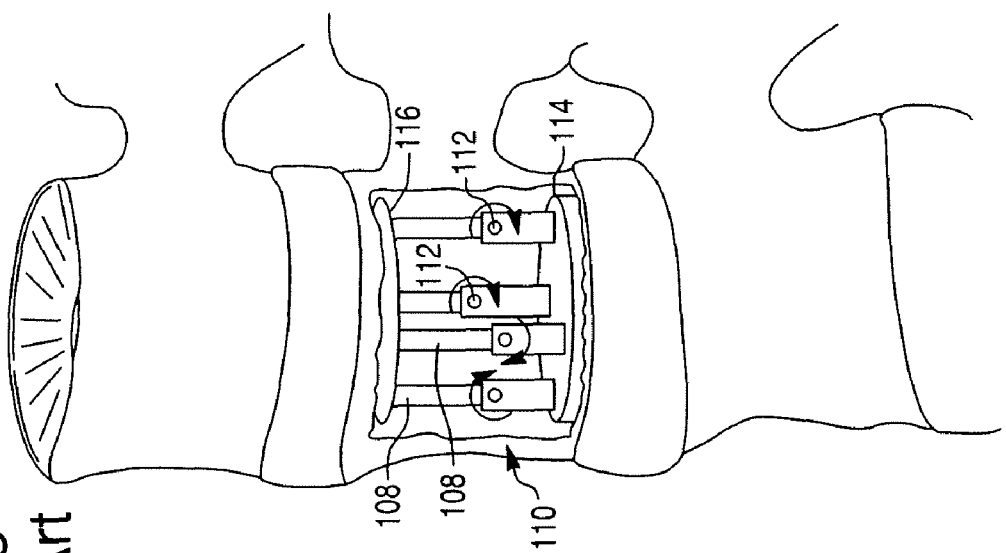
FIG. 13 is a schematic, cut-away side view of a vertebral joint and shows a technique for adjusting the height of an adjustable member implanted in a superior vertebral body.
Figure 16A:
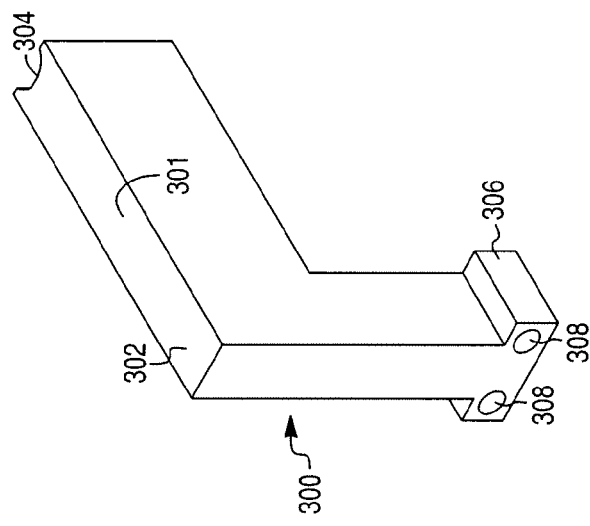
FIGS. 16A-16D are a top perspective view, a first side elevation view, a second side elevation view, and a top plan view, respectively, of the drill guide of FIG. 15A.
Figure 16B:
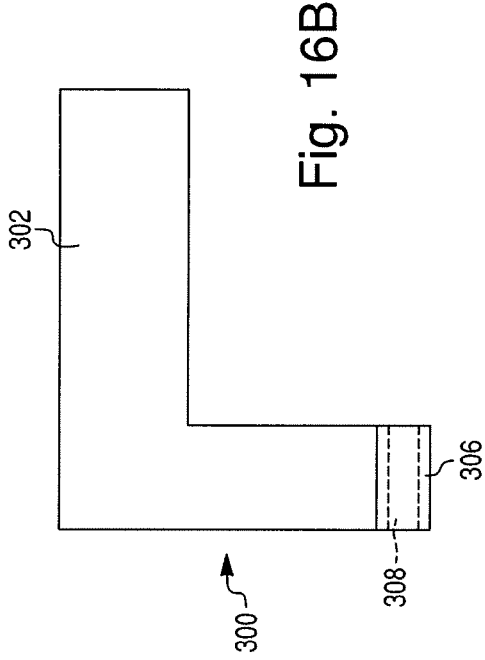
Figure 16D:
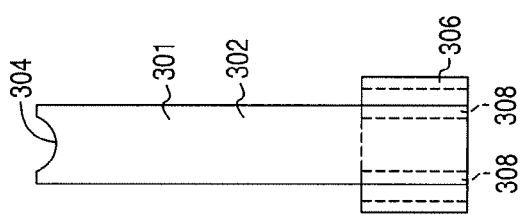
Figure 16C:
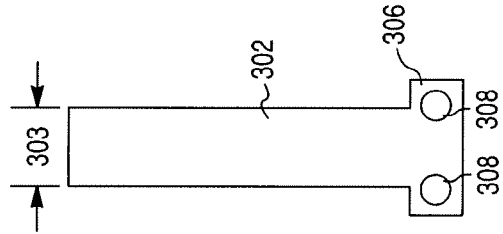

In yet a further aspect of the present invention, the prosthetic device can include spacers 620 to maintain the fixation members 714 at a desired elongated position. The spacers 620 can be used in lieu of the lock screws 63 seen in FIG. 4 and their aforementioned alternatives. FIGS. 23A-23D show an embodiment of a spacer 620 that can be used with fixation members 714. The spacer 620 has a first box portion 622, a second box portion 624, and a peg 626 projecting from the first box portion 622.

In a prosthetic device employing a spacer 620 as shown in FIGS. 21A-21D, the inner plate 752 of the fixation member 714 can have a notch 754, and each plate 842, 844 of the compressible member can have a well 846. The peg 626 of the spacer 620 is configured to pass through the notch 754 and snap into the well 846, to lock the spacer 620 in place in a snap fit, as shown in FIG. 21A. When the peg 626 of the spacer 620 is locked in the appropriate plate 842, 844, the second box portion 624 resides between the adjustment elements 724 of the fixation member 714, as shown in FIG. 21B. The spacers 620 may be configured in varying shapes and of various heights to accommodate different sized vertebrae.

The spacers 620 can be positioned in fixation members 714 after the fixation members 714 are properly positioned in the vertebral bodies. That is, once the fixation members 714 are positioned in the vertebral bodies, the tension or load experienced by the compressible member 818 needs to be adjusted to optimize the normal loading and compression (i.e., the functionality) of the particular disc being replaced.

To optimize the normal loading and compression, a surgeon can use a tensioner, (such as the tensioner described in U.S. Pat. No. 6,761,723) to move the plates 750, 752 of the fixation member 714 toward the endplates of the vertebral body. In this manner, the tensioner may be used to elongate the fixation member 714 until a proper elongation distance between the plates 750, 752 is achieved. As the fixation member 714 elongates, plate 752 contacts and encounters resistance from the compressible member 818. The surgeon can continue to apply a load via the tensioner to the fixation member 714 until a desired corresponding reactive load from the compressible member 818 is reached.

When the applied load measured by the tensioner equals the desired load, the surgeon knows that the fixation member 714 has been lengthened or elongated an appropriate amount to place the compressible member 818 under the proper degree of tension. At this point, the spacer 620 can be inserted into the fixation member 714 until the peg 626 of the spacer 620 snaps in the well 846. As a result, the spacer 60 maintains the fixation member 714 at the appropriate length. The tensioner then can be removed from the fixation member 714.

As an alternative to the spacer 620, the struts 224 can be configured for adjustment like a crutch, that is, by having a hole through an outer casing and a plurality of holes through an adjustable inner member. When the inner member is adjusted to the proper height, a fastener can be inserted through the hole in one side of the casing, through the corresponding hole in the inner member, and then through the hole in the other side of the casing. The fastener immobilizes the inner member with respect to the casing and maintains the proper elongation distance between the upper and lower plates 250, 252 of the fixation member 214.

Clamps also can be used to maintain the proper elongation distance between the plates 250, 252. The clamps can be C-shaped in cross section and have a length equal to the elongation distance. The C-shaped cross section of the clamps leaves a slit or opening along their length. The clamps also are resiliently flexible. When the slit of a clamp is pressed against a strut, the slit widens so that the clamp can be slid around the strut. Once around the strut, the clamp returns to its initial shape. The clamps thus can be positioned on the struts 224 to substantially surround the struts 224 and maintain the proper elongation distance between the plates 250, 252.

A tripod also can be used to maintain the proper distance between the plates 250, 252. The surgeon can select a tripod of an appropriate height, that is, of a height equal to the desired elongation distance, and slide it into the fixation member 214. The surgeon then can position the legs of the tripod on the lower plate 252, preferably against three struts 224, and position the top of the tripod against the upper plate 250.

FIGS. 22A-22D show another embodiment of the prosthetic device 700'. This prosthetic device 700' is similar to the prosthetic device 700 of FIGS. 21A-21D, except that the outer plates 750' of the fixation members 714' of the device 700' shown in FIGS. 22A-22D do not include the risers 753 present on the outer plates 750 of the fixation members 714 of the device 700 shown in FIGS. 21A-21D. All other elements of the fixation members 714', 716' of the device 700' shown in FIGS. 22A-22D are the same as the corresponding elements of the fixation members 714, 716 of the device 700 shown in FIGS. 21A-21D and, therefore, are similarly numbered but include a differentiating apostrophe.

Figure 24:
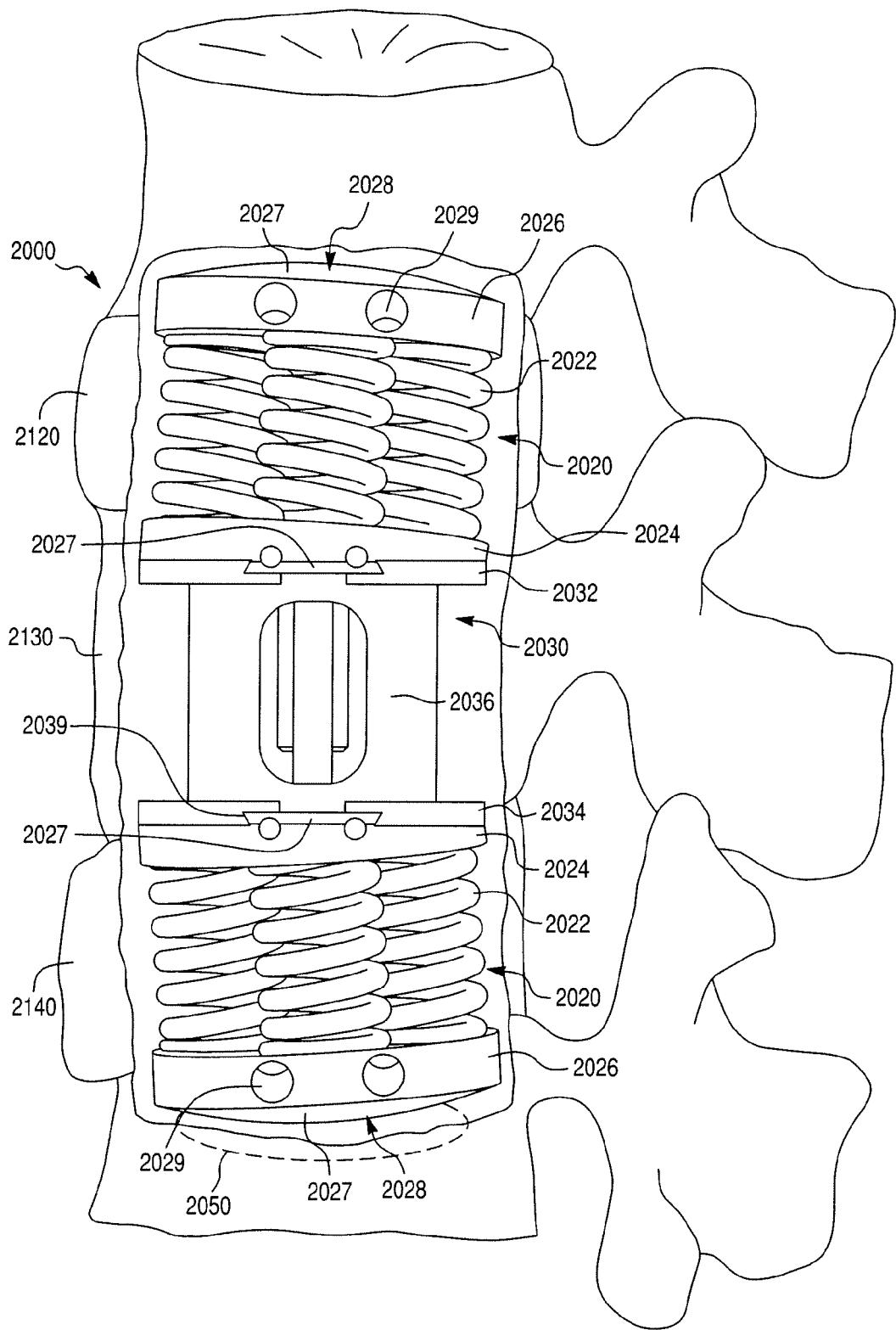
FIG. 24 is a front perspective view of another embodiment of an implantable prosthetic device; the device be shown in a break-away view of a spine.

Another prosthetic device embodiment, which is shown in FIG. 24, restores normal biomechanics and motion of a pair of failing, adjacent intervertebral discs. The prosthetic device 2000 is designed to spare the annulus fibrosis of the discs and the anterior longitudinal ligament of the spine. Moreover, the prosthetic device ensures solid bone fixation via attachment to cancellous vertebral body bone, rather than to the external surface of non-uniform and/or sclerotic vertebral body endplates.

The prosthetic device 2000 may be implanted and adjusted in a procedure that should not take longer than current spinal fusion procedures. Further, it will be understood from the following description that in conjunction with the previously described embodiments, due to its somewhat modular construction, the prosthetic device can be modified to replace more than two intervertebral discs by including an appropriate number of fixation members and compressible members, as needed. A related embodiment of the invention (later discussed in detail) addresses a method of spinal prosthetic implantation by which one or more intervertebral discs may be replaced by an implantable prosthetic device.

The prosthetic device 2000 includes first and second compressible members 2020 and a fixation member 2030 sized to fit within a cavity in the vertebral body 2130 between the first compressible member 2020 and the second compressible member 2020. The first compressible member 2020 is sized to substantially replace the nucleus pulposus of a first intervertebral disc 2120. Similarly, the second compressible member 2020 is sized to substantially replace the nucleus pulposus of a second intervertebral disc 2140 that is separated from the first intervertebral disc 2120 by the vertebral body 2130. In the embodiment shown, the second compressible member 2020 has the same structure as the first compressible member 2020.

Each compressible member 2020 comprises a compressible body portion formed of one or more compressible bodies 2022. The compressible bodies 2022 may be made of a biocompatible material compressible in an axial direction (i.e., in a direction substantially parallel to the spine).

The compressible members 2020 include a first plate 2024 proximal to the fixation member 2030 and a second plate 2026 distal from the fixation member. The second plates 2026 may have sections 2027 having convex surfaces 2028, which may serve as and function like the second fixation member shown in FIG. 7. Further, as later explained in detail, the convex surfaces 2028 may be sized to sit within correspondingly shaped concave seats 2050 formed in the cortical bone endplates of vertebral bodies.

Figure 26:
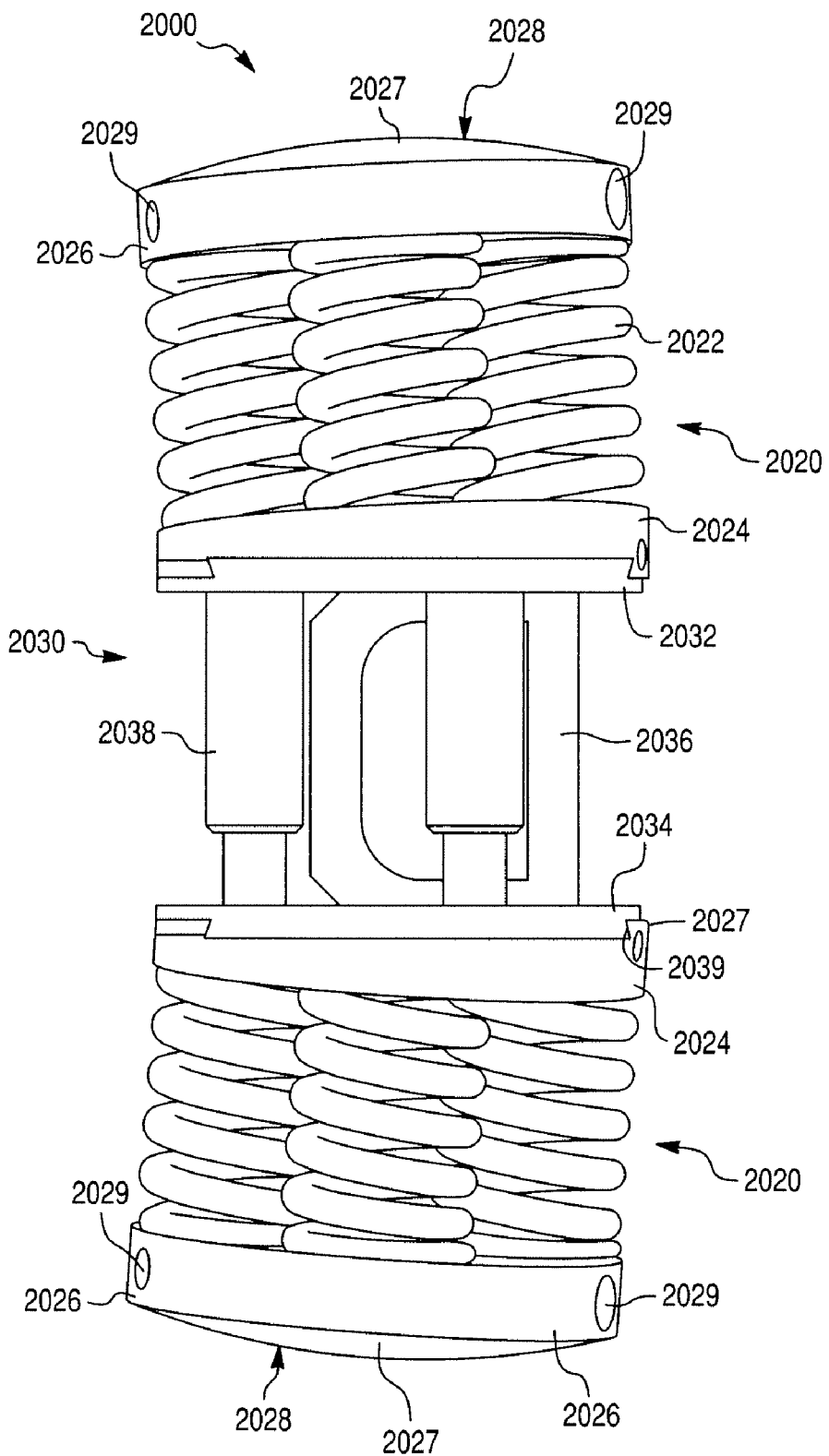
FIG. 26 is a side perspective view of the implantable device of FIG. 24.
Figure 27:
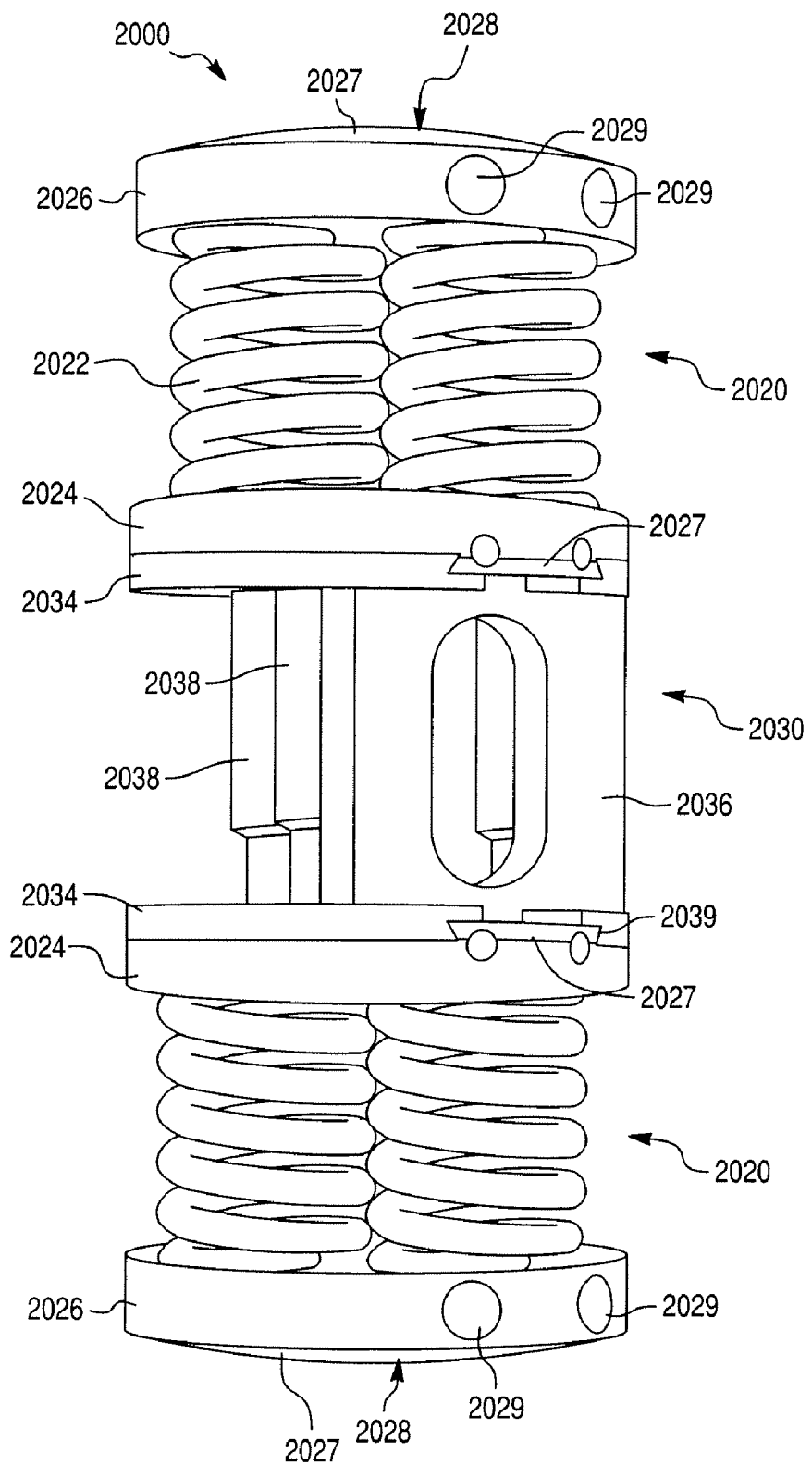
FIG. 27 is another side perspective view of the implantable device of FIG. 24.

The fixation member 2030 may include one or more adjustment members 2038 and/or a locking mechanism, as best shown in FIGS. 26 and 27. The adjustment members 2038 may be telescoping struts, the length of which may be fixed by a locking mechanism such as the c-shaped clamps, tripods, spacers, or other suitable extension devices, as previously discussed. By fixing the height of the fixation member 2030, the locking mechanism fixes the load applied to the fixation member 2030.

Figure 25:
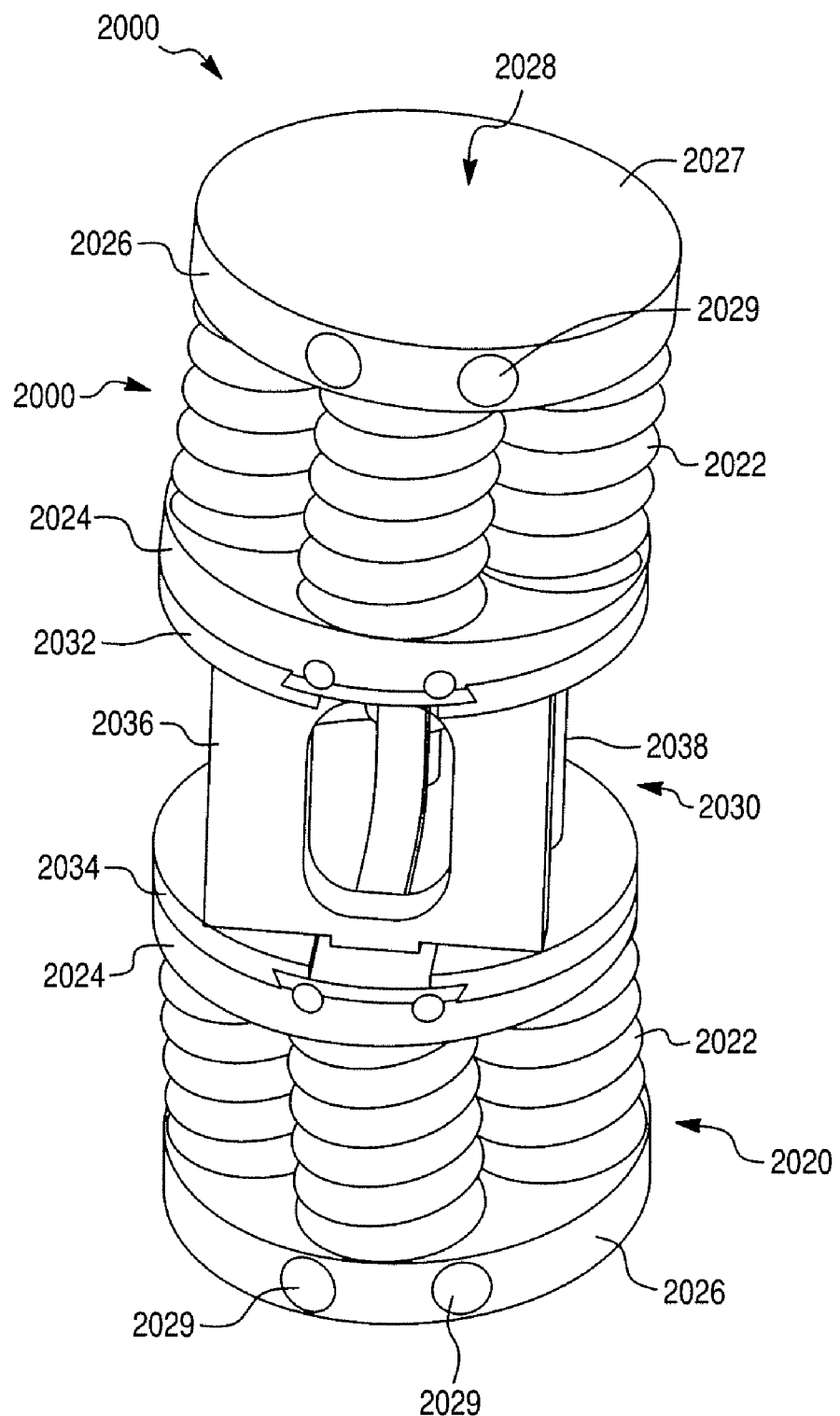
FIG. 25 is a top perspective view of the implantable device of FIG. 24.

Similar to the embodiments previously discussed with respect to FIGS. 15-21, the fixation member 2030 additionally comprises a first plate 2032 and a second plate 2034. The first and second plates 2032, 2034 are configured to engage the first plates 2024 of the compressible members 2020, in a dovetail tenon/mortise relationship. Specifically, as shown in FIGS. 24 and 25, the first plates 2024 have projections 2027 which are sized to engage correspondingly shaped slots 2039 formed in the first and second plates 2032, 2034 of the fixation member 2030. The fixation member 2030 engages the compressible members 2020 by sliding the slots 2039 formed in the first and second plates 2032, 2034 of the fixation member 2030 onto the adjacent correspondingly shaped projections 2027 formed on the first plate 2024 of the compressible members 2020.

If only one intervertebral disc needs to be replaced, the second plate 2034 of the fixation device 2030 can rest against an interior side of the subchondral bone of the endplate of a vertebral body adjacent the failing disc. In this instance, the fixation member 2030 would be positioned in a vertebral body adjacent the failing disc and the compressible member 2020 would be positioned in a failing disc. The second plate 2026 of the compressible member 2020 may sit within a seat 2050 formed in the cortical bone of the vertebral body above the disc.

Figure 28:
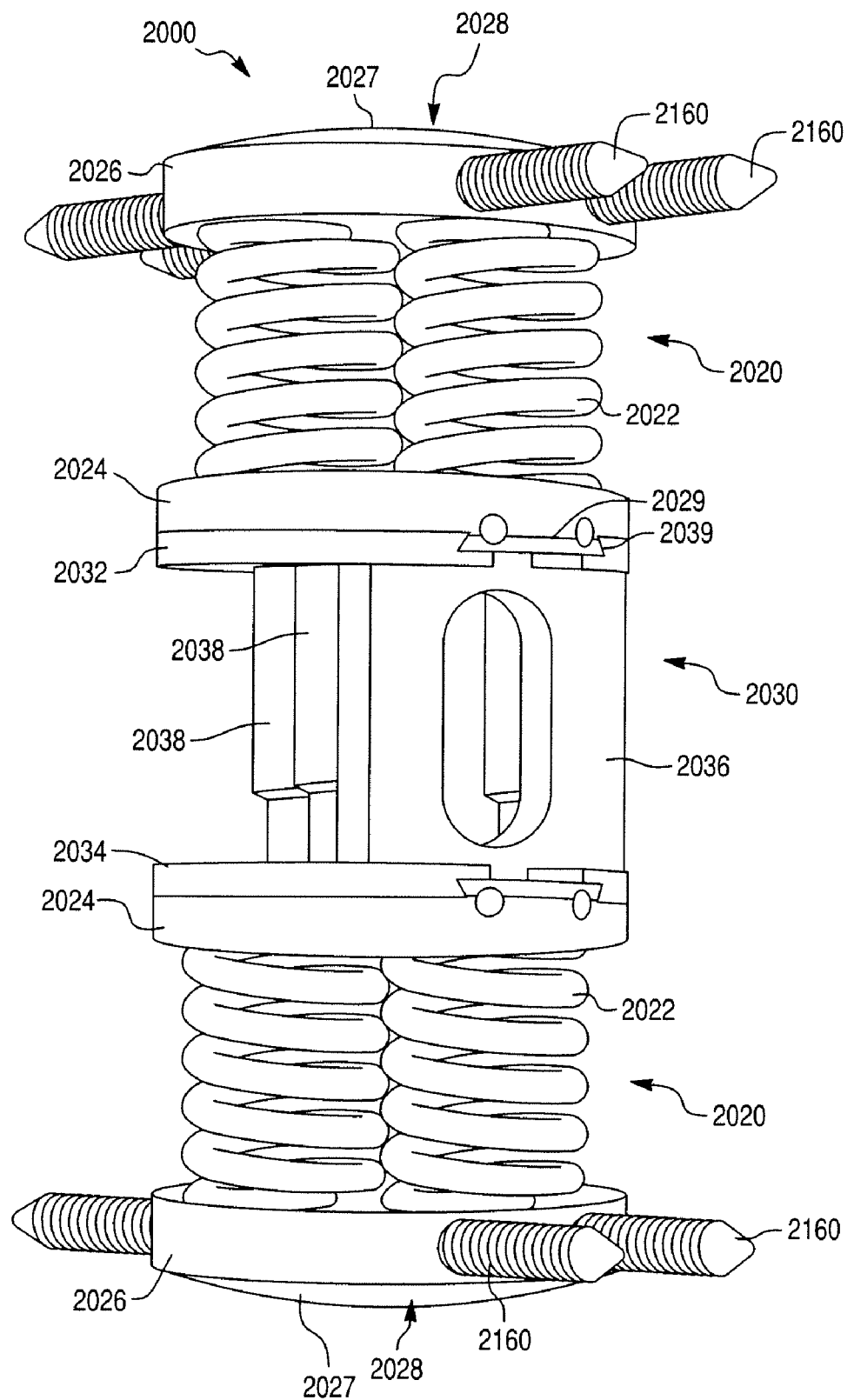
FIG. 28 is a perspective view of the implantable device of FIG. 24 having anchor elements therethrough.

Similar to the aforementioned embodiments, to reduce the risk of subsidence, the compressible members 2020 may include drilling channels 2029 through the second plates 2026. The drilling channels 2029 may be configured to receive anchor elements 2160 (e.g., screws, other fasteners, plates, etc.), as shown in FIG. 28. The anchor elements 2160 may be journalled through the drilling channels 2029 and into the cortical bone of a vertebral body, in the manner previously discussed. As a result, the orientation of the compressible members 2020 with respect to the vertebral body may be additionally stabilized. In addition, either plate of the fixation member 2030 and either plate of the compressible members 2020 can include a tab, as previously discussed, to help minimize subsidence of the prosthetic device.

To implant the prosthetic device 2000, a cavity is created in the vertebral body between the two discs to be reconstructed, in the manner previously described. This procedure, which involves excising bone matter from the vertebral body, can be performed using a cutting guide, a chisel and a chisel guide, and a reamer (such as those described in U.S. Pat. No. 6,761, 723) and/or using surgical implements discussed herein with respect to FIGS. 33-36. Bone harvested from the vertebral body by the reamer can be used after implantation of the prosthetic device to promote bone ingrowth into the prosthetic device, as previously described. This procedure creates a cavity bounded by subchondral bone of the endplates of the vertebral body.

Once the cavity in the vertebral body is formed, an endplate and nucleus cutter attached, for example, to a distractor 920 (shown in FIG. 34B), may be used to cut (which may be in the form of boring) through the first endplate of the vertebral body adjacent the first failing intervertebral disc to be replaced. Once through the endplate, the cutting can continue through the nucleus pulposus of the first failing disc to excise the nucleus pulposus thereof, creating a cavity for a compressible member 2020. In this method, the annulus fibrosis is maintained, although it is envisioned that, if the cutting inadvertently cuts into an inner portion of the annulus fibrosis, the annulus fibrosis still may be capable of securely retaining the compressible member 2020. Additional cutting may be performed into the endplate of the vertebral body on the other side of the first failing intervertebral disc, thereby forming a seat 2050 against which a convex surface 2028 of the compressible member 2020 may be positioned. The seat 2050 will be generally concave in shape so as to better engage the convex surface 2028 of the compressible member 2020.

Once the nucleus pulposus of the first failing intervertebral disc has been excised and the seat 2050 has been formed, the same process may be used to bore through the other endplate of the vertebral body in which the cavity was formed and through the nucleus pulposus of the second failing disc adjacent it. Further, a seat 2050 may be formed in the vertebral body on the other side of the second failing disc.

Once cutting is completed, a first compressible member 2020 is positioned in the cavity in the vertebral body and then pushed through the hole in the endplate and into the space left by the excised nucleus of the first failing disc.

As the first compressible member 2020 is inserted into the first failing disc, the convex surface 2028 is pushed into the seat 2050 in the vertebral body endplate on the other side of the disc. Although the convex surface 2028 may be positioned in cancellous bone in the interior of a vertebral body, it is preferably position in the cortical bone, to help minimize the risk that the second plate 2026 will, over time, undesirably creep into the vertebral body as a result of loading.

Once the first compressible member 2020 is fully implanted, a second compressible member 2020 is inserted into the second failing intervertebral disc in the same manner. Similarly, the convex surface 2028 of the second compressible member 2020 is inserted into the seat 2050 adjacent the second failing disc. It should be readily recognized that the order in which the compressible members 2020 are inserted can be reversed.

Once the compressible members 2020 are in place, the surgeon slides a fixation member 2030 into the cavity in the vertebral body while engaging the projections 2027 of the compressible members 2020 and the slots 2039 in the first and second plates 2032, 2034 of the fixation member 2030. As a result, the fixation member 2030 is fixedly joined to the compressible members 2020. In other embodiments, the compressible members 2020 and the fixation member 2030 may be connected by conventional attachment members, such as screws, or by biocompatible cement or a suitable adhesive composition.

When the fixation member 2030 is in place, the length of the adjustment members 2038 can be adjusted to fix the length of the fixation member 2030, in the manner previously described. Similarly, the length of the fixation member 2030 can be maintained by using a locking mechanism, such as spacer 2036, which prevents further inward adjustment of the adjustment members 2038, as previously described. Alternatively, fixation members can be available in a variety of fixed sizes; a properly sized fixation member could be selected for implantation in the cavity of the vertebral body, thereby negating the need for a locking mechanism. Regardless, when the length of the fixation member 2030 is fixed, the cavity in the vertebral body may be filled with bone graft, as previously described.

To reduce the risk of subsidence, the compressible members 2020 and/or the fixation member 2030 may have drilling channels 2029 for receiving anchor elements 2160 (e.g., screws) to supplement immediate fixation during healing of the bone graft, as previously described.

A porous bone ingrowth coating and/or surface texturing may also be applied to the device. For example, hydroxyapatite or other bone-to-implant chemical or biological interface surface treatment may be applied to the first and second plates 2032, 2034 of the fixation member 2030 and/or to the convex surfaces 2028 (each of which is in contact with bone), to enhance bone growth into a textured porous surface.

If either of the vertebral bodies adjacent the compressible members 20 are scoliotic, the compressible elements 2022 used in the compressible members 2020 may be designed to combat this problem. Specifically, the selected compressible elements 2022 may have spring constants which are greater or less than the spring constants of the remaining compressible elements 2022. As a result, corrective loading on the scoliotic bodies can be better achieved.

Unlike conventional implanted prosthetic devices, which are typically not recommended for replacing two discs, this prosthetic device embodiment 2000 easily replaces the nucleus pulposuses of the intervertebral discs both above and below a vertebral body. Further, not only is this approach more efficient for surgeons, it avoids the problems inherent in separately distracting two disc spaces sufficiently to insert total disc replacements.

Various intervertebral disc prosthetic device embodiments (and the methods of implanting them) have been described. In conjunction with these embodiments, however, various modifications may be used to address a particular patient's condition and/or the level in the spine in which the device will be implanted (e.g., between Lumbar-5 and Sacrum-1 there is a great variation among patients in the shape of the joint). Accordingly, the following describes various alternative compressible member embodiments which may be employed with any of the aforementioned prosthetic device embodiments.

Figure 29A:
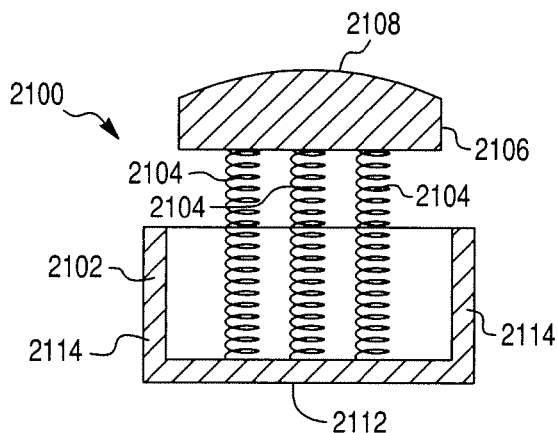
FIGS. 29A and 29B are respective cross-sectional and perspective views of an alternate embodiment compressible member.
Figure 29B:
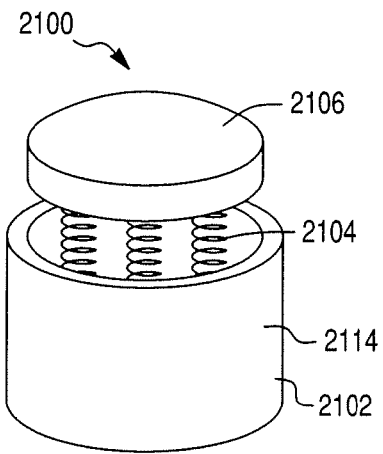
Figure 29E:
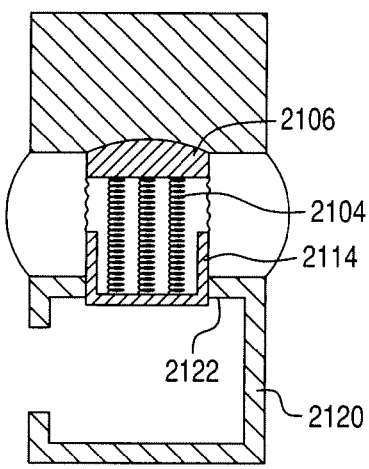
FIG. 29E is a cross-sectional view of either of the embodiments shown in FIGS. 29A-29D implanted in an intervertebral disc.

FIGS. 29A-29E show two alternate embodiments for a compressible member. Specifically, FIGS. 29A and 29B respectively show a cross-sectional view and a perspective view of a compressible member 2100 and FIG. 29E shows the compressible member 2100 positioned in a disc.

The compressible member 2100 is formed of a base member 2102 that may, as shown, be in the shape of a cup. The lower surface 2112 of the base member 2102 may be attached to a fixation member (not shown in FIGS. 29A-29E) in any manner previously discussed (e.g., screws, dovetail tenon/mortise joint, etc.)

A circumferential wall 2114 of the base member 2102, which rises upward from the lower surface 2112, encloses a plurality of compressible elements 2104 (e.g., springs, or any other compressible element previously discussed). As shown in FIG. 29E, the wall 2114, when implanted, compensates for anatomic variations and assures that the endplate 2122 of the vertebral body 2120 engages solid metal.

The other ends of the compressible elements 2104 are attached to an upper member 2106, in a manner similar to the previously described compressible member embodiments. Similarly, the upper member 2106 may have a convex surface 2108 which is configured to rest within a seat 2050 (shown in FIG. 24) formed in a vertebral body endplate, as previously discussed.

Figure 29C:
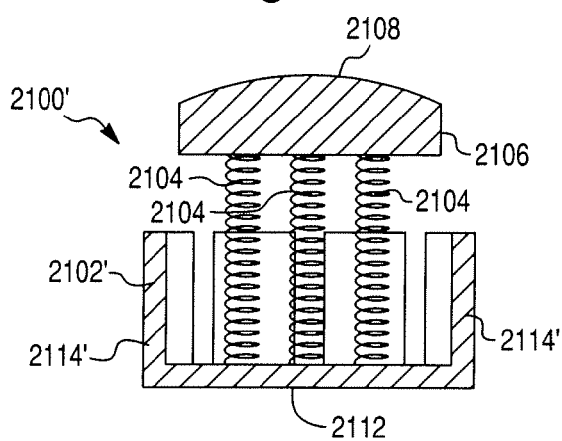
FIGS. 29C and 29D are respective cross-sectional and perspective views of another alternate embodiment compressible member.
Figure 29D:
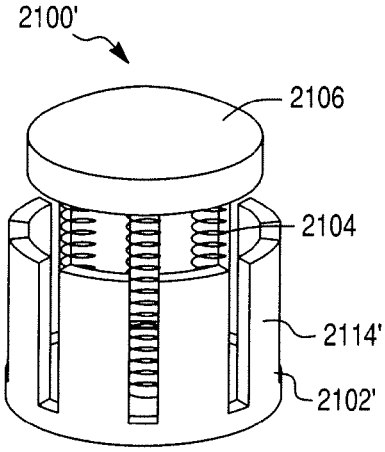

The compressible member embodiment 2100' shown in FIGS. 29C-29D is substantially similar to the compressible member embodiment 2100 shown in FIGS. 29A-29B, except that the wall 2114 in the base member 2102 in the embodiment shown in FIGS. 29A-29B is replaced with a slotted wall 2114' defining an alternative base member 2102'.

The reason for the slotted wall 2114' is that for some individuals and/or some disc locations, additional clearance may serve to facilitate placing the springs over as wide an area as possible. However, as the slots reduce the support and attachment to the cortical bone of the vertebral body, the desires to use certain spring designs and to enhance support/attachment must be weighed in each particular instance.

Figure 30A:
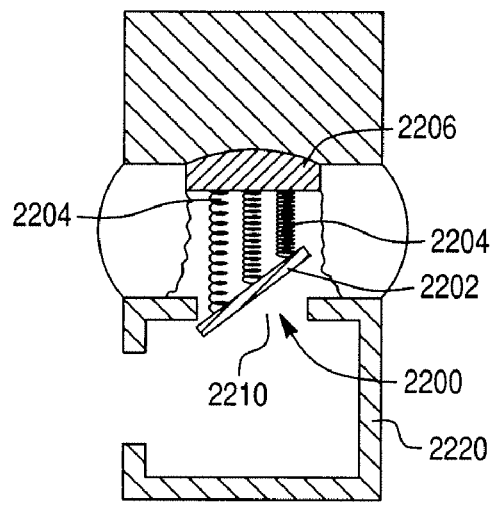
Figure 30B:
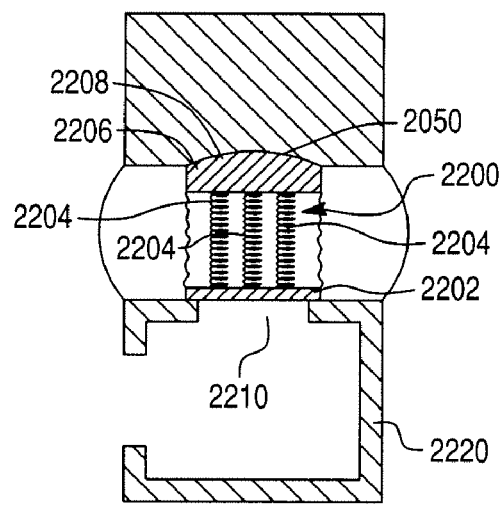

Another compressible member 2200 embodiment is shown in FIGS. 30A-30B. The compressible member 2200 includes a base member 2202, compressible elements 2204, and an upper member 2206. In this embodiment, the base member 2202 is wider than the diameter of the hole 2210 but narrow enough so that it can go through the hole 2210 at an angle after which it can be maneuvered so as to cover the hole 2210, as shown in FIG. 30B. In either case, the base member 2202 rests against the cortical bone of the vertebral body 2220, thereby reducing the likelihood that the compressible member 2200 may experience subsidence into the vertebral body 2220 as a result of cyclical loads applied to the compressible member 2200.

Figure 30C:
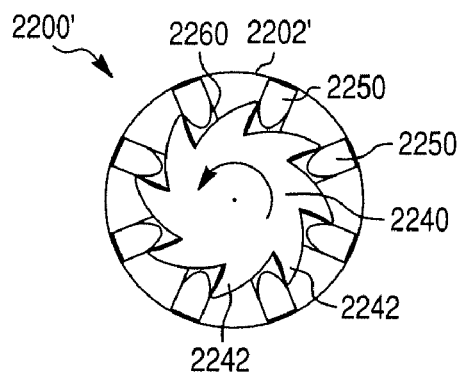
FIGS. 30C and 30D show an alternate embodiment plate that may be used in the embodiment shown in FIGS. 30A and 30B.
Figure 30D:
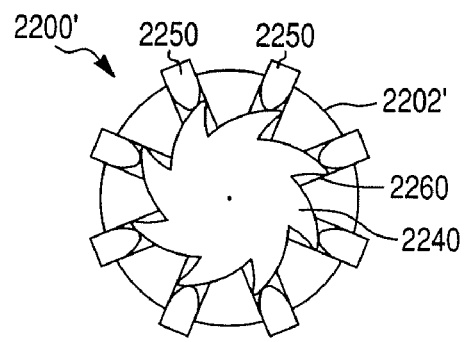

Another compressible member 2200' embodiment is shown in FIGS. 30C and 30D. In this embodiment, the base member 2202' is expandable to be wider than the diameter of the hole 2210 in a vertebral body endplate through which the compressible member 2200' is implanted. Specifically, the base member 2202' includes a rotatable driving plate 2240 and a plurality of radially adjustable leaves 2250. The rotatable plate includes a plurality of projections 2242 that, when the rotatable plate 2240 rotates, push the leaves 2250 radially outward along rails 2260, thereby radially adjusting the overall diameter of the base member 2202'. As a result, after the compressible member 2200' is pushed through the hole 2210, the base member 2202' may be radially expanded to fix the base member 2202' in a manner similar to that shown in FIG. 30B. In addition, although the size of base member 2202' is described as being adjusted by means of leaves, the embodiment is not so limited. Rather, the base member could be adjusted in other ways such as, for example, by means of screws, telescoping rods, etc.

Figure 31:
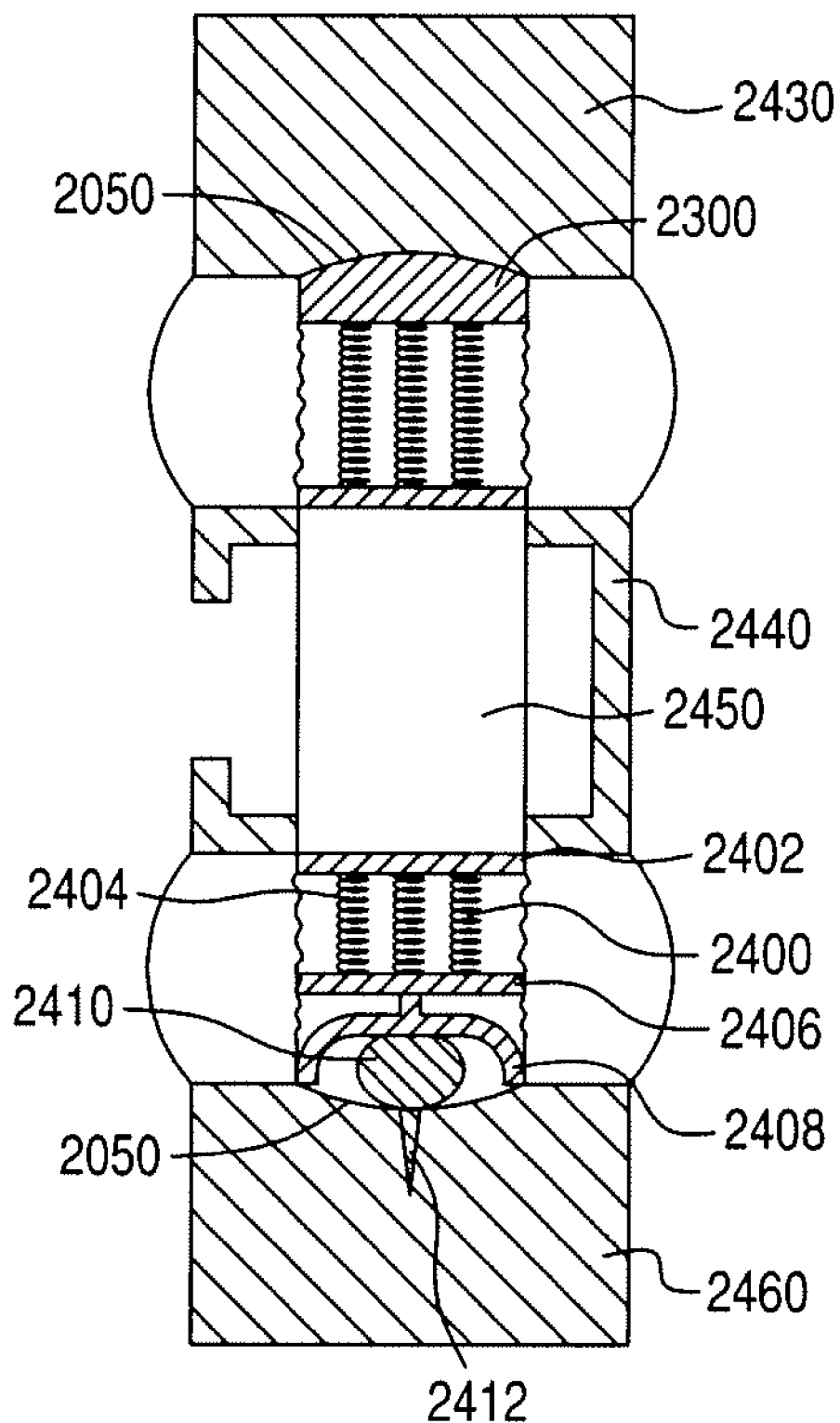
FIG. 31 is a cross-sectional view of two compressible members implanted in intervertebral discs, one of which is another alternate embodiment compressible member.

Another compressible member 2400 embodiment is shown in FIG. 31. A first compressible member 2300, which is provided in a first disc, abuts (along a concave seat 2050) a first vertebral body 2430 and is connected to a fixation member 2440. This first compressible member 2300 and the fixation member 2440 may be any of the compressible member embodiments and fixation member embodiments, respectively, previously discussed. However, it is a second compressible member 2400, which is also connected to the fixation member 2440, which is the focus of FIG. 31. Moreover, although the second compressible member 2400 is shown as being part of a dual compressible member device, it should readily be recognized that it could be incorporated in a single compressible member device.

The second compressible member 2400, like previous embodiments, includes a base member 2402 supporting a plurality of compressible elements 2404. The other ends of the compressible elements 2404 are connected to another plate 2406. Whereas in previous embodiments, the plate 2406 would rest against a vertebral body, in this embodiment, the plate 2406 is attached to a ball-and-socket joint comprised of a socket 2408 and a ball 2410. The socket 2408 is attached to the plate 2406 and the ball 2410 is immobilized in the vertebral body 2460 by means of a spike 2412 or screw.

The purpose of the ball-and-socket connection is to accommodate anatomic variation in which the angle between vertebral endplates may be highly variable among patients. This is particularly helpful between Lumbar-5 and Sacrum-1 where there is a great variation among patients in the shape of the joint and where replacement of two discs (as shown in FIG. 31) in this area is particularly complicated.

It should be readily recognized that the compressible member embodiments 2300, 2400 shown in FIG. 31 can be switched. In other words, the compressible member embodiment 2300 currently adjacent the upper vertebral body 2430 can be switched with the compressible member embodiment 2400 currently adjacent the lower vertebral body 2460.

FIG. 32 shows another embodiment of a compressible member 2500, which like the embodiment 2400 shown in FIG. 31 employs a spike 2512 to immobilize a plate 2506, as hereafter explained in detail. The compressible member embodiment 2500, like previous embodiments, has a base member 2502, an upper member 2506, and a plurality of compressible elements 2504 which extend between the base member 2502 and the upper member 2506.

Whereas in many of the previously described embodiments, the end of a compressible member away from a fixation member was formed to have a convex surface configured to engage a concave seat 2050 formed in a vertebral body, in some instances such an engagement may not provide adequate support for the compressible member. As a result, in the compressible member embodiment 2500 shown in FIG. 32, the plate 2506 adjacent the vertebral body 2520 is formed with a spike 2512 that is configured to penetrate into the vertebral body 2520 so as to immobilize the plate 2506 with respect to the vertebral body 2520. Moreover, the likelihood of subsidence of the compressible member 2500 into the vertebral body 2520 is slight as a result of the remainder of the plate 2506 abutting the cortical bone endplate of the vertebral body 2520.

The aforementioned described various implantable prosthetic devices and the methods by which they may be implanted. In conjunction with these devices and their methods of implantation, this invention also addresses various tools by which the implantation methods may be performed.

Figure 33C:
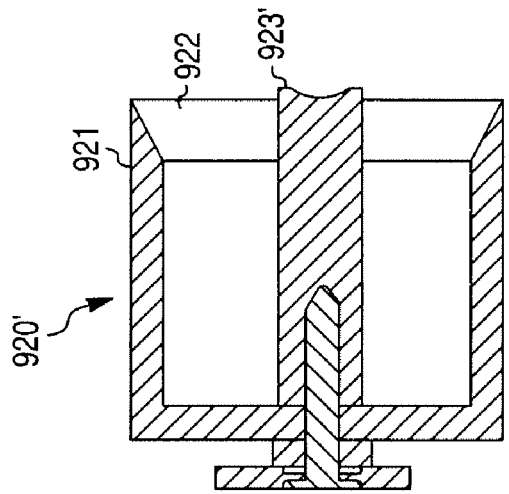
FIG. 33C is a side elevation view, in cross section, of an alternative embodiment of the endplate and nucleus cutter.
Figure 33A:
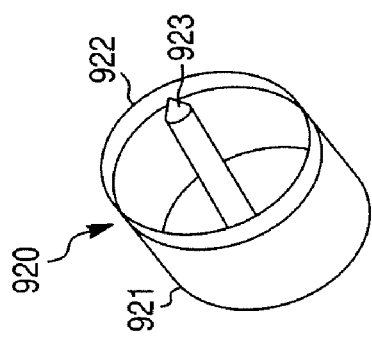
FIGS. 33A and 33B are a top perspective view and a side elevation view (in cross section), respectively, of an endplate and nucleus cutter.
Figure 33B:
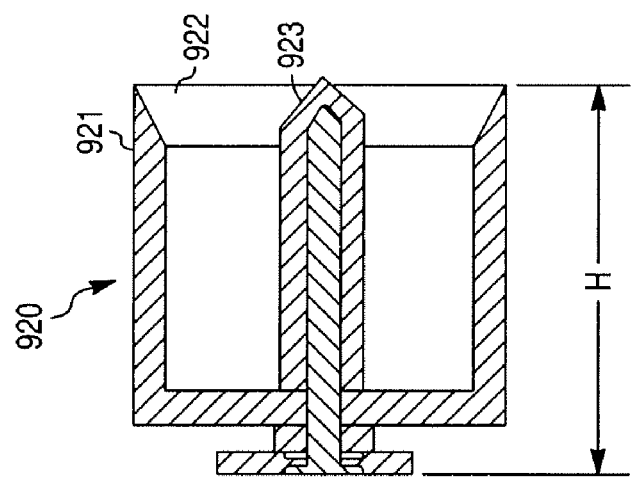

FIGS. 33A-33C illustrate a surgical implement, that is, a cutting implement that can be mounted to a compressor 900 (shown in FIG. 34A) or a distractor 910 (shown in FIG. 34B) to cut through an endplate of a vertebral body and the nucleus pulposus of the intervertebral disc adjacent the vertebral body. The exemplary cutting implement is in the form of an endplate and nucleus cutter 920 having a substantially circular sidewall 921 that terminates in a cutting edge 922.

The maximum diameter of the sidewall 921 of the endplate and nucleus cutter 920 should not be greater than the minimum diameter of the nucleus pulposus and/or the diameter of the prosthesis to be implanted. In addition, the cutting edge 922 can be smooth or, alternatively, serrated. The cutting edge 922 may be thinner than the sidewall 921 and may be tapered to a sharp end. The endplate and nucleus cutter 920 optionally can have a projection 923, as shown in FIG. 33B. The tip of the projection 923 can be used to create a notch in an endplate, thereby bracing the endplate and nucleus cutter 920 relative to the endplate; the projection 923 can serve as an axis of rotation. Moreover, this bracing effect enables a surgeon to cut through the endplate with the sharp end of the endplate and nucleus cutter 920, without risk that the endplate and nucleus cutter 920 will inadvertently slide from its proper position relative to the endplate surface.

An alternative embodiment of the endplate and nucleus cutter 920' is shown in FIG. 33C. The only difference between this embodiment and the one shown in FIG. 33B is that the projection 923' is cylindrical in shape and has a concave end. An advantage of employing the embodiment of FIG. 33C with the embodiment of FIG. 33B on a single compressor 900 is that when the sharp edges of the two endplate and nucleus cutters 920 approach each other, the tip of the projection 923 on the first cutter 920 will be partially journalled into the concave end portion of the projection 923' of the second cutter 920'.

As shown in FIG. 34A, an endplate and nucleus cutter 920 can be attached to an end portion 901 of a first arm 902 of the compressor 900 to face a second arm 904. Similarly, an endplate and nucleus cutter 920, which is attached to an end portion 903 of the second arm 904, faces toward the first arm 902 and toward the other endplate and nucleus cutter 920.

When the handle 905 of the compressor 900 is compressed, the first and second arms 902, 904 move toward each other. In addition, as the first and second arms 902, 904 move toward each other, they maintain their approximately parallel orientation, and the endplate and nucleus cutters 920 approach each other. The endplate and nucleus cutters 920 on the first and second arms 902, 904 can share a common central axis so that, when the handle 905 is fully compressed, the cutting edges 922 of the endplate and nucleus cutters 920 contact each other.

The endplate and nucleus cutters 920 can be either fixedly mounted or rotatably mounted to the arms 902, 904 of the compressor 900. When the endplate and nucleus cutters 920 are fixedly mounted, the surgeon can manually rotate the cutters 920 by swinging the handle 905 of the compressor 900 side-to-side. This side-to-side motion, combined with compression of the handle 905, enables the cutting edges 922 to cut through the endplate and nucleus pulposus of the damaged disc. Alternatively, the endplate and nucleus cutters 920 may be rotatably mounted to the compressor 900. A motor or other drive source can be connected to the cutters 920 to rotate them relative to the arms 902, 904 of the compressor 900.

Figure 35:
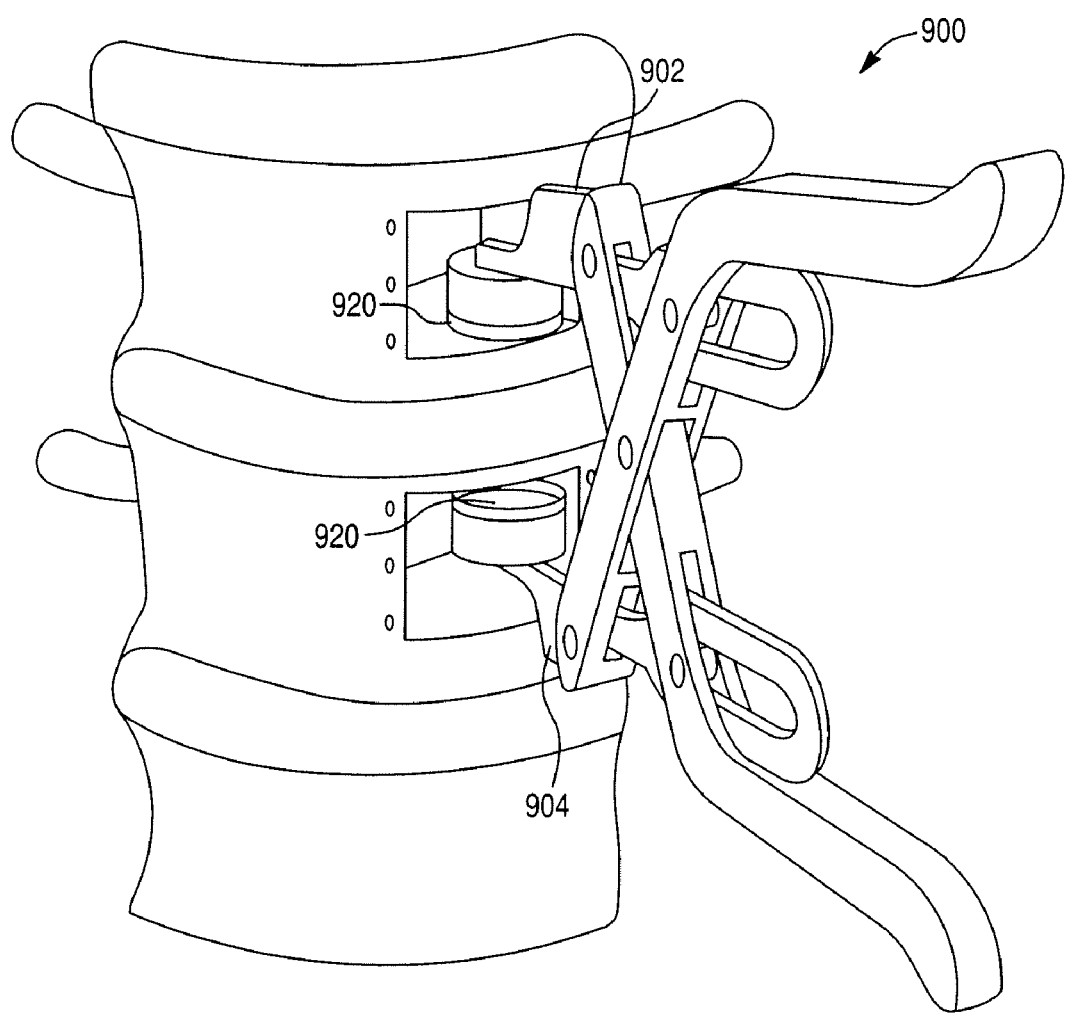
FIG. 35 is a schematic view of a compressor with endplate and nucleus cutters inserted into the cavities of adjacent vertebral bodies.

The compressor 900 can be used when a surgeon wants to implant a prosthetic device having two fixation members, one of which is to go into a vertebral body above a problematic disc and the other of which is to go into the vertebral body below the problematic disc. FIG. 35 shows a compressor 900 being inserted into adjacent vertebral bodies to remove the nucleus pulposus of a damaged disc.

In some situations, however, the surgeon needs to implant only one fixation member (e.g., the embodiments shown in FIGS. 15-18 and 24-28) or only one non-extendable fixation member coupled to a compressible member (e.g., the embodiment shown in FIG. 7). In such situations, a distractor 910 with only one, outwardly facing endplate and nucleus cutter 920 may be used.

FIG. 34B shows a distractor 910 having one endplate and nucleus cutter 920 on a first arm 912 which faces outward and away from a second arm 914. An outwardly facing plate 930 is rotatably attached to the second arm 914 by an axle 931. The plate 930 is designed to be placed against an endplate in a vertebral body and to remain immobile relative to the vertebral body.

As the endplate and nucleus cutter 920 of the distractor 910 either is manually rotated by the surgeon (in an embodiment where the endplate and nucleus cutter 920 is fixedly mounted to the distractor 500) or rotates as a result of a motor (in an embodiment where the endplate and nucleus cutter 920 is rotatably mounted to the distractor 910), the endplate and nucleus cutter 920 will cut through one endplate in a vertebral body, while the plate 930 remains pressed against the other endplate in the vertebral body. The plate 930 will not abrade the vertebral body against which it is placed because it does not rotate with respect to that endplate.

When the arms 912, 914 of the distractor 910 are inserted into a cavity in a vertebral body and the handle 915 is subsequently compressed, the plate 930 will move in one direction to contact the endplate of the vertebral body, and the endplate and nucleus cutter 920 will move in an opposite direction to contact the other endplate of the vertebral body. Continued compression of the handle 915 and rotation of the endplate and nucleus cutter 920 will force the cutter 920 through the endplate and the nucleus pulposus of the adjacent intervertebral disc.

It will be understood that an endplate and nucleus cutter 920 can be mounted to devices having a configuration different than the compressor 900 and distractor 910. For example, an endplate and nucleus cutter 920 can be attached to an end of a single arm, and a surgeon can grip the opposite end of the single arm to position the endplate and nucleus cutter 920 appropriately to cut through the endplate and the nucleus pulposus of a damaged disc. The single arm can be bent to provide additional leverage.

Figure 36D:
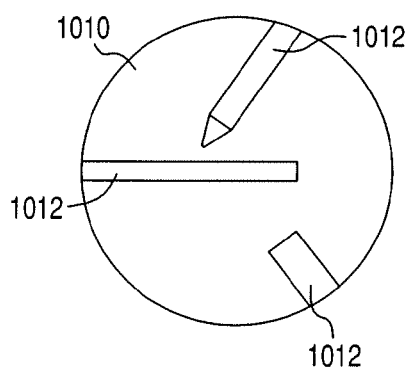
FIGS. 36C and 36D are a top perspective view and a bottom plan view, respectively, of the cutting surface of the endplate and nucleus cutter of FIG. 36A.
Figure 36A:
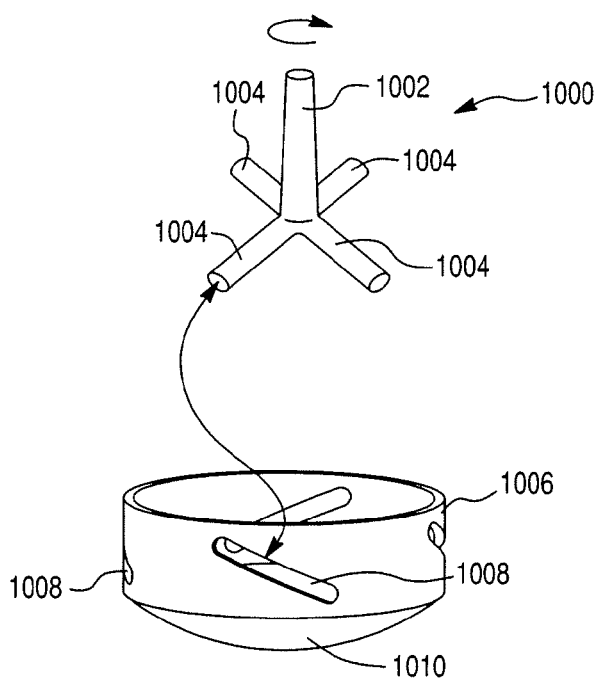
FIG. 36A is a schematic view of an alternative embodiment of the endplate and nucleus cutter in accordance with the invention.
Figure 36B:
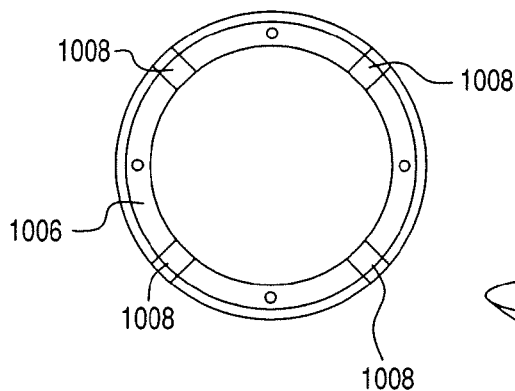
FIG. 36B is a bottom plan view of a main body of the endplate and nucleus cutter of FIG. 36A.
Figure 36C:

FIGS. 36A-36D illustrate another embodiment of an endplate and nucleus cutter 1000. This cutter 1000 includes a rotating axle 1002 with multiple arms 1004, a cylindrical main body 1006 with a pair of oblique slots 1008 to receive the arms 1004 of the axle 1002, and a cutting surface 1010 that attaches to the cylindrical main body 1006. The cutting surface 1010 can have a flat profile or it can have a convex, domed profile as seen in FIGS. 36A, 36C, and 36D. The cutting surface 1010 includes cutting edges 1012 that enable the cutter 1000, when rotated, to cut through the endplate and the nucleus pulposus of the disc.

Figure 36E:
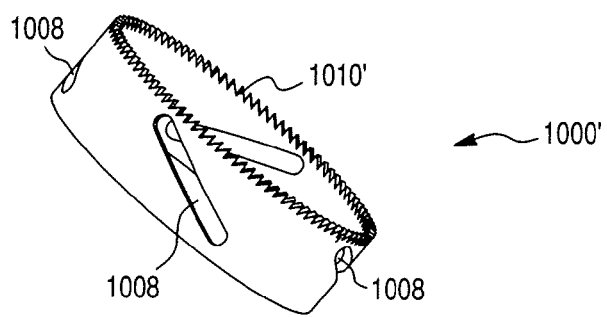
FIG. 36E is a perspective view of another alternative embodiment of the endplate and nucleus cutter.

In another embodiment shown in FIG. 36E, a serrated cutting edge 1010' can be defined around a perimeter of a cup-shaped cutter 1000' which is similar in shaped to the endplate and nucleus cutter 920 shown in FIGS. 33A and 33B.

The cutter 1000 can be mounted to the arm of a compressor or a distractor and, once positioned at a cutting location in a vertebral body, can elongate and move away from the arm. Accordingly, the cutter 1000 can be placed through a relatively small vertebral body window and still reach all the way through the vertebral body endplate and the nucleus pulposus of the damaged disc. When the cutter 1000 is in the shortened position, the arms 1004 of the axle 1002 are positioned in the slots 1008 at a location close to the cutting surface 1010. With rotation of the axle 1002, friction forces the arms 1004 to slide up the slots 1008, which in turn elongates the cutter 1000 and moves the cutting surface 1010 toward the area to be cut.

The intervertebral prosthetic device embodiments of the present invention offer several advantages. For example, the intervertebral prosthetic device embodiments replicate the mechanical properties of a natural intervertebral disc. The intervertebral prosthetic device embodiments restore disc height, defined as the axial distance between vertebrae adjacent the damaged disc, and duplicate the range of motion of a natural intervertebral joint.

As the prosthetic device embodiments have no ball bearings (with the exception of the ball-and-socket joint of the embodiments shown in FIG. 31), rollers, or hinges, the intervertebral prosthetic device embodiments suffer minimal degradation of the prosthetic material and produce minimal wear debris under long-term cyclic loading conditions. Further, the prosthetic device embodiments: (a) can axially compress and thus dissipate energy; (b) may be easily repaired or replaced; (c) may be easily manufactured and implanted by a surgeon; and (d) are durable and modular. Moreover, as the prosthetic device embodiments need not include plastic polymers or elastomeric components, the prosthetic device embodiments do not degrade under long-term cyclic loading conditions.

It should be understood that the benefit of the implantation procedure for the one compressible member/one fixation member embodiment and the dual compressible member/one fixation member embodiments is that only one vertebral body cavity is formed. As a result, both the time necessary for the implantation procedure and the amount of resultant healing are greatly reduced.

Although the previously described embodiments of the intervertebral prosthetic device include an adjustable fixation member, it will be understood that the intervertebral prosthetic device can include a rigid fixation member sized specifically to fit the vertebral body and to adequately pretension the compressible member. Rigid fixation members can be made in various sizes so that a surgeon can select an appropriately sized fixation member for the particular surgical site.

The prosthetic device embodiments can comprise biocompatible metallic materials, such as a titanium alloy having, for example, 4% vanadium and 6% aluminum. Persons of skill in the art will recognize other suitable materials, for example, a cobalt-chromium alloy, such as alloy number 301. Alternatively, the prosthetic device embodiments, with the exception of the springs of the compressible member, can comprise a ceramic material, such as aluminum oxide or zirconium oxide. The porous surfaces of the fixation members can be coated with hydroxyapatite or bioactive proteins (e.g., bone morphogenic protein) to encourage bone ingrowth.

The fixation members of the prosthetic device embodiments, which may be composed of carbon fiber polyetheretherketone, bone graft (auto- or allo-graft bone), bone cement, etc., support the compressible member(s) until the bone graft (which is packed into the open space of the fixation members) heals. Once the bone graft heals, however, the fixation members may no longer be needed. Accordingly, the fixation members of the prosthetic device embodiments may be composed of a bioresorbable material that would gradually be replaced by bone over time. Suitable bioresorbable materials to form the fixation members include structural allograft (bank) bone, or polymers made of polylactic acid or polyglycolic acid. Similarly, the anchor members also can be made of carbon fiber or of a bioresorbable material, such as polylactic acid, polyglycolic acid, or a combination of those materials.

The compressible members may be, for example, springs, elastomers, monolithic bodies, elastic polymers, hydrogels, disc allograft, or any other material which displays similar mechanical properties when placed under stress (i.e., tension and/or compression) and which substantially regains its original shape upon removal of the stress.

The embodiments of the prosthetic device previously described have advantages over conventional devices. For example, although the prosthetic device may be implanted using a straight anterior approach, it may be implanted using an anterolateral approach to the spine that is a retroperitoneal approach in the plane between the abdominal vessels and the psoas muscle.

Unlike the conventional and more dangerous straight anterior approach required by total disc replacement devices (which sever the anterior longitudinal ligament and/or sever the annulus fibrosis, both of which disrupt tissues that will not heal), the embodiments described herein only disrupt bone material in the adjacent vertebral body and the nucleus pulposus in the intervertebral disc. The bone heals and the nucleus pulposus is replaced by the prosthetic device.

Further, the embodiments of the prosthetic device described herein minimally infringe upon areas of the vertebral body which would be used to provide a fusion should that later become necessary. Specifically, by maintaining the anterior longitudinal ligament, the anterolateral approach helps maintain spinal function and stability. In addition, an anterolateral approach on one side of a vertebral body allows for a later opposite side approach for adjustment of the device or for adjacent level disc replacement should that become necessary. Further, this opposite side approach would not be hindered by scar tissue from the previous procedure.

The prosthetic device embodiments also allow for bending and torsion motion, as well as axial displacement and elastic compression. Further, unlike an articulated joint, the prosthetic device deforms similarly to a normal, healthy disc. Moreover, unlike previous total disc replacement devices which may result in motion of about 3.8° to 4.6°, the embodiments of the invention herein described maintain the motion at a nearly healthy level of motion, i.e., about 7° to about 12°.

The ability to pretension the fixation member allows for a more precise restoration of disc height. Further, as the fixation members may be anchored entirely to cancellous bone, at least some embodiments avoid problems inherent to poor bony ingrowth, which may result from sclerotic endplates. As a result, the risk of device loosening is minimized. And, as the device is enclosed entirely by bone and the annulus fibrosis, ejection, dislocation, and migration of the device is very unlikely. In addition, intramedullary fixation of the fixation member in the vertebral body provides greater stability. The fixation member is provided within the cancellous bone of a vertebral body adjacent the failing disc(s), to maximize the osteogenic potential of bone to grow into the fixation member. Further, the replacement of the autologous bone removed from the vertebral body during the procedure (or the addition of bone cement) into the open vertebral body facilitates the transfer of loads to the cortical bone walls of the vertebral body once the bone heals.

Moreover, fibrous soft tissue growth into the compressible members will fill the normal volume of the disc nucleus. As a result, as the compressible member is compressed, this tissue will bulge outward and radially load the inner annulus fibrosis in a manner similar to a healthy nucleus. The radially outward loading will restore the function of the retained annulus fibrosis.

Finally, the prosthetic device embodiments may be used no matter how collapsed a patient's disc may be. An overdistraction problem inherent for installation of total disc replacements does not arise with respect to the prosthetic device described herein.

The preferred embodiments have been set forth herein for the purpose of illustration. This description, however, should not be deemed to be a limitation on the scope of the invention.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A prosthetic device for treating first and second intervertebral discs, the prosthetic device comprising:
   a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;
   a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member in place;
   a fixation member sized to fit within a cavity in the vertebral body between the first and second compressible members and configured to maintain a fixed length after implantation; and
   a releasable connection that connects at least one of the first and second compressible members to the fixation member,
   wherein the fixation member comprises a plurality of adjustable members and a wedge-shaped member.

2. The prosthetic device of claim 1, wherein the fixation member includes first and second plates; and wherein each of the first and second compressible members include an outer plate, an inner plate positioned between the outer plate and the fixation member and one or more compressible elements positioned between the inner and outer plates.

3. The prosthetic device of claim 2, wherein the releasable connection connects the inner plate of one of the first and second compressible members to a corresponding one of the first and second plates of the fixation member.

4. The prosthetic device of claim 3, wherein the releasable connection includes openings, on one of the first and second plates of the fixation member, that are shaped to engage corresponding projections on a corresponding one of the inner plates of the first and second compression members.

5. The prosthetic device of claim 3, wherein the releasable connection includes projections, on one of the first and second plates of the fixation member, that are shaped to engage corresponding slots on a corresponding one of the inner plates of the first and second compression members.

6. The prosthetic device of claim 2, wherein the compressible elements comprise a biocompatible material compressible in an axial direction.

7. The prosthetic device of claim 2, wherein the outer plates of each of the first and second compressible members include a convex surface, wherein each convex surface is sized to sit within correspondingly shaped concave seats formed in cortical bone endplates of vertebral bodies.

8. The prosthetic device of claim 2, wherein the fixation member further comprises a locking mechanism configured to maintain the adjustable members at a fixed length and wherein the adjustable members are configured to adjust a length of the fixation member.

9. The prosthetic device of claim 8, wherein the locking mechanism is a spacer.

10. The prosthetic device of claim 9, wherein the spacer is configured to snap fit to the adjustable members and/or one of the plates of the fixation member.

11. The prosthetic device of claim 9, wherein the spacer includes a projection to engage with an opening in one of the plates of the fixation member.

12. The prosthetic device of claim 8, wherein the adjustable members are telescoping struts.

13. The prosthetic device according to claim 1, further comprising at least one anchor element configured to immobilize and/or stabilize the compressible member and/or the fixation member.

14. The prosthetic device according to claim 1, wherein the fixation member comprises:
   an outer member configured to be placed against bone of the vertebral body;
   an inner member opposite the outer member; and
   a longitudinal axis extending between the outer and inner members,
   wherein the outer member includes a tab extending outward along an axis different from the longitudinal axis.

15. The prosthetic device according to claim 1, wherein the fixation member comprises at least one adjustable member and a wedge-shaped member.

16. The prosthetic device of claim 1, wherein the fixation member includes a porous bone ingrowth surface.

17. A prosthetic device for treating first and second intervertebral discs, the prosthetic device comprising:
   a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;
   a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member in place; and
   a fixation member sized to fit within a cavity in the vertebral body between the first and second compressible members and configured to maintain a fixed length after implantation,
   wherein at least one of the first compressible member and second compressible member includes a plurality of compressible elements and the at least one of the first compressible member and second compressible member is open on lateral sides to permit fibrous tissue to grow on and between the compressible elements, and
   wherein the fixation member comprises a plurality of adjustable members and a wedge-shaped member.

18. The prosthetic device of claim 17, wherein the fixation member includes first and second plates; and wherein the plurality of compressible elements of the first and second compressible members are positioned between an outer plate and an inner plate positioned between the outer plate and proximal to the fixation member.

19. The prosthetic device of claim 18, wherein the first and second plates of the fixation member includes a porous ingrowth surface for bony fixation.

20. The prosthetic device of claim 18, wherein the adjustable members are configured to adjust a length of the fixation member, and wherein the adjustable members and the inner and outer plates of the first and second compressible members include a porous ingrowth surface for bony fixation.

21. The prosthetic device of claim 18, wherein the inner and outer plates of the first and second compressible members include a biocompatible coating for bony fixation.

22. The prosthetic device of claim 18, wherein the compressible elements comprise a biocompatible material compressible in an axial direction.

23. The prosthetic device of claim 18, wherein the outer plates of each of the first and second compressible members include a convex surface, wherein each convex surface is sized to sit within correspondingly shaped concave seats formed in cortical bone endplates of vertebral bodies.

24. The prosthetic device of claim 17, wherein the fixation member further comprises a locking mechanism configured to maintain the adjustable members at a fixed length and wherein the adjustable members are configured to adjust a length of the fixation member.

25. The prosthetic device of claim 24, wherein the locking mechanism is a spacer.

26. The prosthetic device of claim 24, wherein the at least one adjustable is a members are telescoping struts.

27. The prosthetic device of claim 17, wherein the fixation member includes a porous bone ingrowth surface.

28. A prosthetic device for treating first and second intervertebral discs, the prosthetic device comprising:
a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;
a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member n place; and
a fixation member sized to fit within a cavity in the vertebral body between the first and second compressible members and configured to maintain a fixed length after implantation,
wherein the fixation member comprises a plurality of adjustable members and a wedge-shaped member, and
wherein the adjustable members and the fixation member are open on lateral sides to permit bone tissue to grow on and between the adjustable members.

29. The prosthetic device of claim 28, wherein the fixation member includes first and second plates; and wherein each of the first and second compressible members include an outer plate, an inner plate positioned between the outer plate and the fixation member and one or more compressible elements positioned between the inner and outer plates.

30. The prosthetic device of claim 29, wherein the first and second plates of the fixation member includes a porous ingrowth surface for bony fixation.

31. The prosthetic device of claim 29, wherein the inner and outer plates of the first and second compressible members include a porous ingrowth surface for bony fixation.

32. The prosthetic device of claim 29, wherein the inner and outer plates of the first and second compressible members include a biocompatible coating for bony fixation.

33. The prosthetic device of claim 29, wherein the compressible elements comprise a biocompatible material compressible in an axial direction.

34. The prosthetic device of claim 29, wherein the outer plates of each of the first and second compressible members include a convex surface, wherein each convex surface is sized to sit within correspondingly shaped concave seats formed in cortical bone endplates of vertebral bodies.

35. The prosthetic device of claim 28, wherein the fixation member further comprises:
a locking mechanism configured to maintain the adjustment adjustable members at a fixed length.

36. The prosthetic device of claim 35, wherein the locking mechanism is a spacer.

37. The prosthetic device of claim 28, wherein the adjustable members are telescoping struts.

38. The prosthetic device of claim 28, wherein the fixation member includes a porous bone ingrowth surface.

39. A prosthetic device for treating first and second intervertebral discs, the prosthetic device comprising:
a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;
a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member in place; and
a fixation member sized to fit within a cavity in the vertebral body between the first and second compressible members and configured to maintain a fixed length after implantation,
wherein the fixation member includes a first member, a second member spaced from the first member, adjustable members that extend from the first member to the second member and a wedge-shaped member, wherein the adjustable members are configured to permit free movement of the first member relative to the second member for the adjustment of spacing between the first member and the second member along a longitudinal axis of the fixation member, and the adjustable members are configured to prevent movement of the first member relative to the second member along a latitudinal axis of the fixation member.

40. The prosthetic device of claim 39, wherein adjustment in the longitudinal direction of the fixation member adjusts a measurable tension in one of the first and second compressible members.

41. The prosthetic device of claim 40, wherein the adjustable members include a plurality of telescoping struts.

42. The prosthetic device of claim 39, wherein the fixation member further comprises:
a locking mechanism configured to maintain the adjustable members at a fixed length.

43. The prosthetic device of claim 39, wherein the adjustable members include telescoping struts.

44. The prosthetic device of claim 39, wherein the fixation member includes a porous bone ingrowth surface.

45. A prosthetic device for treating first and second intervertebral discs, the prosthetic device comprising:
a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;
a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member in place; and a fixation member sized to fit within a cavity in the vertebral body between the first and second compressible members and configured to maintain a fixed length after implantation, wherein at least one of the first compressible member and second compressible member is configured and connected so as to be fixed in position at an interface with another portion of the prosthetic device, and wherein the fixation member comprises a plurality of adjustable members and a wedge-shaped member.

46. The prosthetic device of claim 45, wherein each of the first and second compressible members include an outer plate, an inner plate positioned between the outer plate and the fixation member, and one or more compressible elements positioned between the inner and outer plates.

47. The prosthetic device of claim 46, wherein deformation of the one or more compressible elements permits change of the relative positions of the inner plate and outer plate of the first compressible member.

48. The prosthetic device of claim 45, wherein the at least one first and second compressible member is configured and connected to be nonarticulating at the interface with the other portion of the prosthetic device.

49. The prosthetic device of claim 45, wherein the fixation member includes a porous bone ingrowth surface.

50. A prosthetic device for treating first and second intervertebral discs, the prosthetic device comprising:

a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;

a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member in place;

a fixation member sized to fit within a cavity in the vertebral body between the first and second compressible members and configured to maintain a fixed length after implantation; and a wedge-shaped support member disposed between the fixation member and one of the first and second compressible members, wherein the fixation member comprises a plurality of adjustable members and the wedge-shaped support member.

51. The prosthetic device of claim 50, wherein the support member includes a first surface facing the fixation member and a second surface facing the one of the first compressible member and second compressible member, wherein the first and second surfaces are oblique, and wherein a circumferential surface around the support member varies in width.

52. The prosthetic device of claim 50, wherein the fixation member includes a porous bone ingrowth surface.

53. A prosthetic device for treating first and second intervertebral discs, the prosthetic device comprising:

a first compressible member sized to substantially replace the nucleus pulposus of the first intervertebral disc and to be surrounded by and substantially maintain the annulus fibrosis of the first intervertebral disc so that the annulus fibrosis can retain the first compressible member in place;

a second compressible member sized to substantially replace the nucleus pulposus of the second intervertebral disc, that is separated from the first intervertebral disc by a vertebral body, and to be surrounded by and substantially maintain the annulus fibrosis of the second intervertebral disc so that the annulus fibrosis can retain the second compressible member in place; and a fixation member sized to fit within a cavity in the vertebral body between the first and second compressible members and configured to maintain a fixed length after implantation, wherein at least one of the first compressible member and second compressible member includes a plurality of compressible elements, wherein at least one of the compressible elements has a different characteristic from another of the compressible elements to provide corrective loading on a malaligned spine, and wherein the fixation member comprises a plurality of adjustable members and a wedge-shaped member.

54. The prosthetic device of claim 53, wherein at least one of the compressible elements has a different characteristic from another of the compressible elements to provide corrective loading on scoliotic vertebral bodies.

55. The prosthetic device of claim 53, wherein the at least one of the compressible elements has a spring constant which is greater or less than the spring constants of the another of the compressible elements.

56. The prosthetic device of claim 55, wherein the at least one of the first compressible member and second compressible member has asymmetric compression under an axial load.

57. The prosthetic device of claim 53, wherein the fixation member includes a porous bone ingrowth surface.

* * * * *

UNITED STATES PATENT AND TRADEMARK OFFICE
CERTIFICATE OF CORRECTION

PATENT NO. : 8,057,549 B2  Page 1 of 1
APPLICATION NO. : 11/948427
DATED : November 15, 2011
INVENTOR(S) : Glenn Robin Buttermann, Jeffrey Joseph Anderman and Frank Robert Ferris, Jr.

It is certified that error appears in the above-identified patent and that said Letters Patent is hereby corrected as shown below:

Title Page

Item (75) Inventors: Please change "Glenn Robin Butterman, Mahtomedi, MN (US)" to --Glenn Robin Buttermann, Mahtomedi, MN (US)--

Signed and Sealed this
Thirteenth Day of March, 2012

David J. Kappos
*Director of the United States Patent and Trademark Office*